US009873916B2

(12) United States Patent
Myomoto et al.

(10) Patent No.: US 9,873,916 B2
(45) Date of Patent: Jan. 23, 2018

(54) METHOD FOR PREDICTING RESPONSE TO TRASTUZUMAB THERAPY IN BREAST CANCER PATIENTS

(75) Inventors: Akira Myomoto, Kamakura (JP); Satoko Kozono, Kamakura (JP); Fumiaki Sato, Kyoto (JP); Masakazu Toi, Kyoto (JP); Takayuki Ueno, Kyoto (JP); Zhipeng Wang, Kyoto (JP); Gozoh Tsujimoto, Kyoto (JP); Kazuharu Shimizu, Kyoto (JP)

(73) Assignees: TORAY INDUSTRIES, INC., Tokyo (JP); KYOTO UNIVERSITY, Kyoto (JP)

(\*) Notice: Subject to any disclaimer, the term of this patent is extended or adjusted under 35 U.S.C. 154(b) by 268 days.

(21) Appl. No.: 14/113,776

(22) PCT Filed: Apr. 25, 2012

(86) PCT No.: PCT/JP2012/061100
§ 371 (c)(1),
(2), (4) Date: Oct. 24, 2013

(87) PCT Pub. No.: WO2012/147800
PCT Pub. Date: Nov. 1, 2012

(65) Prior Publication Data
US 2014/0073533 A1   Mar. 13, 2014

(30) Foreign Application Priority Data
Apr. 25, 2011   (JP) ................. 2011-097432

(51) Int. Cl.
*C12Q 1/68*   (2006.01)
*A61K 39/395*   (2006.01)
*C07K 16/32*   (2006.01)
*A61K 39/00*   (2006.01)

(52) U.S. Cl.
CPC ...... *C12Q 1/6886* (2013.01); *A61K 39/39558* (2013.01); *C07K 16/32* (2013.01); *A61K 2039/505* (2013.01); *C12Q 2600/106* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| 5,990,299 A | * | 11/1999 | Ruzdijic | ............ | C12N 15/1138 536/23.1 |
| 2005/0266420 A1 | * | 12/2005 | Pusztai | ................ | C12Q 1/6883 435/6.16 |
| 2008/0076674 A1 | | 3/2008 | Litman et al. | | |
| 2011/0015080 A1 | * | 1/2011 | Golub | .................. | C12Q 1/6834 506/2 |
| 2013/0065778 A1 | * | 3/2013 | Weidhaas | ............... | C12N 15/111 506/9 |
| 2014/0147495 A1 | | 5/2014 | Croce et al. | | |

FOREIGN PATENT DOCUMENTS

| CN | 101341259 A | 1/2009 |
| JP | 2008-535482 A | 9/2008 |
| JP | 2010-504350 A | 2/2010 |
| JP | 2010-94075 A | 4/2010 |
| JP | 2010-510964 A | 4/2010 |
| WO | WO 2006/098978 A1 | 9/2006 |
| WO | WO 2008/036741 A2 | 3/2008 |
| WO | WO 2008/036776 A2 | 3/2008 |
| WO | WO 2009/080437 A9 | 7/2009 |
| WO | WO 2009/148593 A1 | 12/2009 |
| WO | WO 2011/094335 A2 | 8/2011 |
| WO | WO 2011/135459 A2 | 11/2011 |

OTHER PUBLICATIONS

Thomson et al. Nature. 2004. 1(1): pp. 1-7 and supplementary Figure 1.*
Singh et al Proceedings of the New Zealand Society of Animal Production. 2004. 64: 8-1.*
Saetre et al Molecular Brain Research. 2004. 126:198-206).*
Heggard et al International Journal of Cancer. May 4, 2011. 102. 130: 1378-1386.*
Palmer et al. BMC Genomics. 2006. 7:115.*
Zhou et al Scientific Reports. Jun. 10, 2015. 6:11251.*
Murphy et al. Pathology, 2005, vol. 37(4), pp. 271-277.*
Liu et al Clinical Immunology. 2004. 112: 225-230.*
Coleman et al. Drug Discovery Today. 2003. 8: 233-235.*
Search Report dated Jan. 23, 2015 for European Application No. 12777416.4.
Practice Guideline for Breast Cancer [1] Drug Therapy, 2010, the Japanese Breast Cancer Society (ed). pp. 1-5, with partial translation.
Buzdar et al., "Significantly higher pathologic complete remission rate after neoadjuvant therapy with trastuzumab, paclitaxel, and epirubicin chemotherapy: results of a randomized trial in human epidermal growth factor receptor 2-positive operable . . . ," JCO, vol. 23, No. 16, Jun. 1, 2005, pp. 3676-3685.
Nagata et al., "PTEN activation contributes to tumor inhibition by trastuzumab, and loss of PTEN predicts trastuzumab resistance in patients," Cancer Cell, vol. 6, Aug. 2004, pp. 117-127
Scaltriti et al., "Cyclin E amplification/overexpression is a mechanism of trastuzumab resistance in HER2+ breast cancer patients," PNAS Early Edition, Medical Sciences, 2011, pp. 1-6.
Scott et al., "Coordinate Suppression of ERBB2 and ERBB3 by Enforced Expression of Micro-RNA miR-125a or miR-125b," The Journal of Biological Chemistry, vol. 282, No. 2, Jan. 12, 2007, pp. 1479-1486.
Végran et al., "Gene expression profile and response to trastuzumab-docetaxel-based treatment in breast carcinoma," British Journal of Cancer, vol. 101, No. 8, 2009, pp. 1357-1364.
Vogel et al., "Efficacy and safety of trastuzumab as a single agent in first-line treatment of HER2—Overexpressing metastatic breast cancer," Journal of Clinical Oncology, vol. 20, No. 3, Feb. 1, 2002, pp. 719-726.

\* cited by examiner

*Primary Examiner* — Carla Myers
(74) *Attorney, Agent, or Firm* — Birch, Stewart, Kolasch & Birch, LLP

(57) ABSTRACT

This invention relates to a composition and a method for prediction of a response to Trastuzumab therapy in a breast cancer patient, and more specifically, a composition, a kit, a DNA chip, and a method for predicting a response to Trastuzumab therapy by using polynucleotides each comprising a nucleotide sequence represented by any of SEQ ID NOs: 1 to 9, 11 to 19, and 21 to 23 in the Sequence Listing or a nucleotide sequence derived therefrom by substitution of u with t, mutants thereof, derivatives thereof, or fragments thereof comprising at least 16 continuous nucleotides, or a polynucleotide comprising a complementary sequence thereof, and using an increase or decrease in Her2 protein expression level as an indicator.

2 Claims, 3 Drawing Sheets

Fig. 3

SEQUENCE LISTING

<160> NUMBER OF SEQ ID NOS: 23

<210> SEQ ID NO 1
<211> LENGTH: 22
<212> TYPE: RNA
<213> ORGANISM: Homo sapiens

<400> SEQUENCE: 1
ucggccugac cacccacccc ac                                        22

<210> SEQ ID NO 2
<211> LENGTH: 18
<212> TYPE: RNA
<213> ORGANISM: Homo sapiens

<400> SEQUENCE: 2
uucacaggga ggugucau                                             18

<210> SEQ ID NO 3
<211> LENGTH: 22
<212> TYPE: RNA
<213> ORGANISM: Homo sapiens

<400> SEQUENCE: 3
ugaaacauac acgggaaacc uc                                        22

<210> SEQ ID NO 4
<211> LENGTH: 22
<212> TYPE: RNA
<213> ORGANISM: Homo sapiens

<400> SEQUENCE: 4
uucaaguaau ccaggauagg cu                                        22

<210> SEQ ID NO 5
<211> LENGTH: 22
<212> TYPE: RNA
<213> ORGANISM: Homo sapiens

<400> SEQUENCE: 5
ugagguagua gguuguauag uu                                        22

<210> SEQ ID NO 6
<211> LENGTH: 22
<212> TYPE: RNA
<213> ORGANISM: Homo sapiens

<400> SEQUENCE: 6
ugagguagua gguugugugg uu                                        22

<210> SEQ ID NO 7
<211> LENGTH: 22
<212> TYPE: RNA
<213> ORGANISM: Homo sapiens

<400> SEQUENCE: 7
ugagguagua guuuguacag uu                                        22

<210> SEQ ID NO 8
<211> LENGTH: 21
<212> TYPE: RNA
<213> ORGANISM: Homo sapiens

<400> SEQUENCE: 8

-continued aaggcagggc ccccgcuccc c                                        21

<210> SEQ ID NO 9
<211> LENGTH: 21
<212> TYPE: RNA
<213> ORGANISM: Homo sapiens

<400> SEQUENCE: 9
gcccuccgcc cgugcacccc g                                        21

<210> SEQ ID NO 10
<211> LENGTH: 24
<212> TYPE: RNA
<213> ORGANISM: Homo sapiens

<400> SEQUENCE: 10
ucccugagac ccuuuaaccu guga                                     24

<210> SEQ ID NO 11
<211> LENGTH: 23
<212> TYPE: RNA
<213> ORGANISM: Homo sapiens

<400> SEQUENCE: 11
uaauacugcc ggguaaugau gga                                      23

<210> SEQ ID NO 12
<211> LENGTH: 22
<212> TYPE: RNA
<213> ORGANISM: Homo sapiens

<400> SEQUENCE: 12
ugagguagga gguuguauag uu                                       22

<210> SEQ ID NO 13
<211> LENGTH: 20
<212> TYPE: RNA
<213> ORGANISM: Homo sapiens

<400> SEQUENCE: 13
ucacaccugc cucgccccc                                           20

<210> SEQ ID NO 14
<211> LENGTH: 22
<212> TYPE: RNA
<213> ORGANISM: Homo sapiens

<400> SEQUENCE: 14
ugagguagua gguuguaugg uu                                       22

<210> SEQ ID NO 15
<211> LENGTH: 23
<212> TYPE: RNA
<213> ORGANISM: Homo sapiens

<400> SEQUENCE: 15
cucucaccac ugcccuccca cag                                      23

<210> SEQ ID NO 16
<211> LENGTH: 22
<212> TYPE: RNA
<213> ORGANISM: Homo sapiens

<400> SEQUENCE: 16
uccuucauuc caccggaguc ug                                            22

<210> SEQ ID NO 17
<211> LENGTH: 23
<212> TYPE: RNA
<213> ORGANISM: Homo sapiens

<400> SEQUENCE: 17
guccaguuuu cccaggaauc ccu                                           23

<210> SEQ ID NO 18
<211> LENGTH: 23
<212> TYPE: RNA
<213> ORGANISM: Homo sapiens

<400> SEQUENCE: 18
aacauucaac gcugucggug agu                                           23

<210> SEQ ID NO 19
<211> LENGTH: 23
<212> TYPE: RNA
<213> ORGANISM: Homo sapiens

<400> SEQUENCE: 19
caacggaauc ccaaaagcag cug                                           23

<210> SEQ ID NO 20
<211> LENGTH: 22
<212> TYPE: RNA
<213> ORGANISM: Homo sapiens

<400> SEQUENCE: 20
ucccugagac ccuaacuugu ga                                            22

<210> SEQ ID NO 21
<211> LENGTH: 22
<212> TYPE: RNA
<213> ORGANISM: Homo sapiens

<400> SEQUENCE: 21
uauugcacuu gucccggccu gu                                            22

<210> SEQ ID NO 22
<211> LENGTH: 22
<212> TYPE: RNA
<213> ORGANISM: Homo sapiens

<400> SEQUENCE: 22
agagguagua gguugcauag uu                                            22

<210> SEQ ID NO 23
<211> LENGTH: 21
<212> TYPE: RNA
<213> ORGANISM: Homo sapiens

<400> SEQUENCE: 23
aucacauugc cagggauuuc c                                             21

METHOD FOR PREDICTING RESPONSE TO TRASTUZUMAB THERAPY IN BREAST CANCER PATIENTS

TECHNICAL FIELD

The present invention relates to a composition useful for prediction (or determination, evaluation, detection, or diagnosis) of the response to Trastuzumab therapy in breast cancer patients, to a method for predicting (or determining, evaluating, detecting, or diagnosing) the response to Trastuzumab therapy in breast cancer patients using the composition, and to a kit for prediction (or determination, evaluation, detection, or diagnosis) of the response to Trastuzumab therapy in breast cancer patients using the composition.

BACKGROUND ART

Breast cancer is a disease characterized by the malignancy of cells in the mammary tissue and the random growth of the malignant cells. It is said that this cancer develops in a morbidity of 1 in 25-30 women in Japan or 1 in 8-10 women in Europe and the United States. It is also known that men suffer from breast cancer although the morbidity is low. From recent studies, it has been found that patients with breast cancer are composed of a variety of populations with different biological characteristics, and responses to treatment and prognosis significantly vary among patients of different populations. Specifically, it is suggested that breast cancer can be roughly classified into five molecular subtypes through the comprehensive gene expression analysis on DNA chips. In routine clinical practice, however, breast cancer is often classified into four subtypes by detecting the expression of estrogen receptor, progesterone receptor, and Her2 protein, so that the treatment plan can be determined based thereon. In principle, the treatment to breast cancer is performed by means of surgical therapy, and chemotherapy and radiation therapy are further employed in combination depending on cancer staging, metastasis, general conditions, and classified breast cancer subtypes. When providing chemotherapy, it is particularly important to evaluate a drug(s) to be administered to a target patient and to select an appropriate treatment plan, depending on the breast cancer subtype as described above (Non-Patent Document 1).

Among these subtypes, Her2-positive breast cancer, which accounts for approximately 25% of all breast cancer cases, shows a high degree of malignancy, a high rate of metastasis, and a poor prognosis. Accordingly, improvement in the outcome of treatment of Her2-positive breast cancer remains crucial in the future.

Trastuzumab (tradename: Herceptin®, Chugai Pharmaceutical, Co., Ltd.) is an antibody drug approved by the Ministry of Health, Labor, and Welfare in Japan, which exerts an anti-tumor effect by binding to Her2 protein on the surface of Her2-positive breast cancer cells. Trastuzumab is the first-line agent that was used for treatment of Her2-positive breast cancer. However, some patients with Her2-positive breast cancer show no response to Trastuzumab (which means that Trastuzumab is not effective), and some patients develop serious side effects, such as cardiac failure, respiratory difficulty, or allergies as a result of Trastuzumab administration. In current clinical diagnosis, whether or not the breast cancer is Her2-positive is determined by detecting the overexpression of Her2 protein and/or the amplification of a gene for Her2 protein on the genome by immunohistochemical means. With these techniques, however, patients who have Her2-positive breast cancer but show no response to Trastuzumab or patients who may develop side effects cannot be identified.

Specifically, it is known that the percentage of patients showing response to Trastuzumab was 35% or lower among patients that had the overexpression of Her2 protein detected by immunohistochemical means and were treated with a single agent, i.e. Trastuzumab alone (Non-Patent Document 2). In methods for examining whether breast cancer is Her2-positive by detecting the overexpression of Her2 protein by immunohistochemical means or by detecting the amplification of a gene for Her2 protein on the genome (which is an examination method as disclosed in Non-Patent Document 3), the percentage of patients showing response to Trastuzumab is known to be 65.2% or lower among patients who were subjected to treatment with Trastuzumab in combination with another anti-tumor agent (Non-Patent Document 3). More specifically, the accuracy for prediction of Trastuzumab response as determined by the examination method of Non-Patent Document 3, which is currently employed in clinical sites, is at most 65.2%.

Drug therapy for treatment of breast cancer has achieved remarkable progression in recent years, and it is becoming possible to select a variety of therapeutic agents depending on cancer properties. In such situation, if the response to Trastuzumab therapy in breast cancer patients could be predicted with higher accuracy than is possible with the method that is currently employed to identify the Her2-positive breast cancer, the method for treatment of a patient with Her2-positive breast cancer could be selected more easily and, as a result, chemotherapy effects could be maximized while side effects could be minimized.

Reports on the response to Trastuzumab therapy in patients with Her2-positive breast cancer that have been made in the past are: activation of PTEN protein (Non-Patent Document 4); gene amplification and/or overexpression of cyclin E (Non-Patent Document 5); and control of Her2 protein expression with miR-125a and/or miR-125b (Non-Patent Document 6).

Non-Patent Document 4 discloses that PTEN expression levels in a patient with Her2-positive breast cancer is evaluated by an immunohistochemical technique, that cells in which PTEN expression is suppressed are less susceptible to Trastuzumab-mediated growth inhibition, and that the PTEN expression level is correlated with inhibition of disease progression in a patient with Her2-positive breast cancer by Trastuzumab.

Non-Patent Document 5 discloses the evaluation of cyclin E protein expression levels in patients with Her2-positive breast cancer responsive to Trastuzumab therapy by immunohistochemical means, and that the percentage of patients who have not experienced disease progression was higher in the groups of patients showing higher cyclin E protein expression levels among patients who have been subjected to treatment with Trastuzumab and other anticancer agents.

Non-Patent Document 6 discloses that elevated miR-125a and miR-125b expression levels lead to lowered expression levels of Her2 protein, which is targeted by Trastuzumab.

It is also known that the expression levels of let-7a (Patent Document 1), let-7b (Patent Document 1), and miR-145 (Patent Document 2) are lowered in breast cancer patients, and the expression level of miR-200c (Patent Document 3) is elevated in breast cancer patients.

PRIOR ART DOCUMENTS

Patent Documents

Patent Document 1: US 2008/0076674 A1
Patent Document 2: JP 2010-510964 A
Patent Document 3: JP 2010-504350 A Non-Patent Documents Non-Patent Document 1: "Practice Guidelines for Breast Cancer [1]Drug Therapy, 2010," the Japanese Breast Cancer Society (ed.), page 2, line 15 to page 5, line 1, the 3$^{rd}$ edition, Kanehara Shuppan Co. (Tokyo, Japan), published Jun. 24, 2010
Non-Patent Document 3: A. U. Buzdar et al., 2005, Journal of Clinical Oncology, Vol. 23, pp. 3676-3685
Non-Patent Document 4: Yoichi, N. et al., 2004, Cancer Cell, Vol. 6, pp. 117-127
Non-Patent Document 5: Maurizio, S. et al., 2011, Proc. Natl. Acad. Sci., U.S.A., Early Edition, pnas. 1014835108
Non-Patent Document 6: Scott, G. K. et al., 2007, J. Biol. Chem., Vol. 282, pp. 1479-1486

SUMMARY OF THE INVENTION

Problem to be Solved by the Invention

As described above, a plurality of genes and proteins exhibiting expression levels that are correlated with response to Trastuzumab therapy as a consequence of such therapy were known in the prior art. However, sufficient values of such genes or proteins as markers for predicting response to Trastuzumab therapy in a patient with Her2-positive breast cancer have not been found.

Concerning PTEN as described in the Non-Patent Document 4, it is impossible to predict the response to Trastuzumab therapy in respective breast cancer patients from PTEN expression levels before Trastuzumab administration. Also, concerning cyclin E as described in Non-Patent Document 5, it is impossible to predict the response to Trastuzumab therapy in respective breast cancer patients from cyclin E protein expression levels. Further, concerning miR-125a and miR-125b as described in Non-Patent Document 6, the correlation between the increase in expression levels of miR-125a and miR-125b and the response to Trastuzumab therapy in patients with Her2-positive breast cancer is not known, and thus, no such markers enable the prediction of the response to Trastuzumab therapy in respective breast cancer patients. Accordingly, such expression levels have not been employed as indicators in general clinical settings, and markers that enable more accurate prediction of the response to Trastuzumab therapy in breast cancer patients have been desired.

Objects of the present invention are to provide: a composition useful for prediction (or determination, evaluation, detection, or diagnosis) of the response to Trastuzumab therapy in a breast cancer patient, a method for predicting (or determining, evaluating, detecting, or diagnosing) the response to Trastuzumab therapy in a breast cancer patient using the composition, and a kit for prediction (or determination, evaluation, detection, or diagnosis) of the response to Trastuzumab therapy in a breast cancer patient using the composition.

Means for Solving Problem

Gene markers for prediction of the response to Trastuzumab therapy in breast cancer patients can be screened for by, for example, comparing amounts of genes, proteins, or metabolites contained in tissues, body fluids, or secretion products removed at the time of examination, before treatment, during treatment, or after treatment from breast cancer patients who have been treated with Trastuzumab or with Trastuzumab in combination with another anticancer agent and who respond to Trastuzumab therapy, with those of patients who do not respond to Trastuzumab therapy.

In recent years, DNA-chip-based analysis of gene expression levels has been commonly used as a method for searching for markers. On a DNA chip, probes that utilize nucleotide sequences corresponding to several hundreds to several tens of thousands of gene species are immobilized. When samples to be tested are applied to such a DNA chip, genes contained in the samples bind to probes, and the binding amounts may be measured by certain means to determine the amounts of genes in the samples. Genes corresponding to the probes immobilized on DNA chip can be freely selected. Also, the gene expression levels in samples may be compared using samples such as issues, FFPE specimens, body fluids, or secretion products removed at the time of examination, before treatment, during treatment, or after treatment from breast cancer patients, so that genes that can function as markers for diagnosis of breast cancer can be presumed.

In order to solve the above-mentioned problems, the present inventors analyzed the expression levels of genes in breast cancer lesions obtained from breast cancer patients before therapy using needle biopsy, thereby having now found genes usable as markers for prediction of the response to Trastuzumab therapy in breast cancer patients, and having now also found that the expression levels of such genes in the breast cancer lesions are decreased or reduced, or increased or elevated, in breast cancer patients exhibiting high response to Trastuzumab therapy. This has led to the completion of the present invention.

1. SUMMARY OF THE INVENTION

The present invention includes the following features.

According to the first aspect, the present invention provides a composition for use in prediction of a response to Trastuzumab therapy in a breast cancer patient, which comprises two or more polynucleotides selected from the group consisting of polynucleotides, mutants thereof, or fragments thereof of the following (a) to (j).

(a) polynucleotides each consisting of a nucleotide sequence represented by represented by any of SEQ ID NOs: 1 to 9, 11 to 19, and 21 to 23 or a nucleotide sequence derived therefrom by substitution of u with t, mutants thereof, derivatives thereof, or fragments thereof comprising at least 16 continuous nucleotides;

(b) polynucleotides each comprising a nucleotide sequence represented by represented by any of SEQ ID NOs: 1 to 9, 11 to 19, and 21 to 23 or a nucleotide sequence derived therefrom by substitution of u with t;

(c) polynucleotide each consisting of a nucleotide sequence complementary to the nucleotide sequence represented by represented by any of SEQ ID NOs: 1 to 9, 11 to 19, and 21 to 23 or to a nucleotide sequence derived therefrom by substitution of u with t, mutants thereof, derivatives thereof, or fragments thereof comprising at least 16 continuous nucleotides;

(d) polynucleotides each comprising a nucleotide sequence complementary to the nucleotide sequence represented by represented by any of SEQ ID NOs: 1 to 9, 11 to 19, and 21 to 23 or to a nucleotide sequence derived therefrom by substitution of u with t; and (e) polynucleotides each hybridizing under stringent conditions to any of the polynucleotides (a) to (d), or fragments thereof comprising at least 16 continuous nucleotides.

(f) polynucleotides each consisting of the nucleotide sequence represented by represented by any of SEQ ID NOs: 10 and 20 or a nucleotide sequence derived therefrom by substitution of u with t, mutants thereof, derivatives thereof, or fragments thereof comprising at least 16 continuous nucleotides;

(g) polynucleotides each comprising the nucleotide sequence represented by any of SEQ ID NOs: 10 and 20 or a nucleotide sequence derived therefrom by substitution of u with t;

(h) polynucleotides each consisting of a nucleotide sequence complementary to the nucleotide sequence represented by represented by any of SEQ ID NOs: 10 and 20 or to a nucleotide sequence derived therefrom by substitution of u with t, mutants thereof, derivatives thereof, or fragments thereof comprising at least 16 continuous nucleotides;

(i) polynucleotides each comprising a nucleotide sequence complementary to the nucleotide sequence represented by any of SEQ ID NOs: 10 and 20 or to a nucleotide sequence derived therefrom by substitution of u with t; and (j) polynucleotides each hybridizing under stringent conditions to any of the polynucleotides (f) to (i), or fragments thereof comprising at least 16 continuous nucleotides.

According to the second aspect, the present invention provides a kit for prediction of a response to Trastuzumab therapy in a breast cancer patient comprising two or more polynucleotides of the polynucleotides, mutants thereof, derivatives thereof, and/or fragments thereof, as described in (a) to (e) above.

According to an embodiment, the kit further comprises one or two polynucleotides of the polynucleotides, mutants thereof, derivatives thereof, and/or fragments thereof, as described in (f) to (j) above.

In the kit as described above, the two or more polynucleotides are polynucleotides each consisting of a nucleotide sequence represented by any of SEQ ID NOs: 1 to 23 or a nucleotide sequence derived therefrom by substitution of u with t, polynucleotides each consisting of a complementary sequence thereof, polynucleotides each hybridizing under stringent conditions to such polynucleotide, or fragments thereof comprising at least 16 continuous nucleotides.

According to another embodiment, the two or more polynucleotides are packaged in different containers separately or in any combination.

According to the third aspect, the present invention provides a DNA chip for prediction of a response to Trastuzumab therapy in a breast cancer patient comprising two or more polynucleotides of the polynucleotides, mutants thereof, derivatives thereof, and/or fragments thereof, as defined in (a) to (e) above.

According to an embodiment, the DNA chip further comprises one or two polynucleotides of the polynucleotides, mutants thereof, derivatives thereof, and/or fragments thereof, as described in (f) to (j) above.

According to the fourth aspect, the present invention provides a method for predicting a response to Trastuzumab therapy of a breast cancer patient, comprising measuring expression levels of two or more target nucleic acids corresponding to the above-described composition in a sample from a breast cancer patient, and predicting, determining, or evaluating in vitro a breast cancer patient's response to Trastuzumab therapy.

According to an embodiment, the method comprises using the kit according to the second aspect of the present invention.

According to another embodiment, the method comprises using the DNA chip according to the third aspect of the present invention.

According to the fifth aspect, the present invention provides a method for predicting a response to Trastuzumab therapy of a breast cancer patient, comprising the following steps of:

(1) measuring in vitro expression levels of target nucleic acids in a plurality of samples from breast cancer patients who are known to respond to Trastuzumab therapy using any composition above, any kit above, any DNA chip above, or a combination thereof;

(2) measuring expression levels of the target nucleic acids obtained in step (1) and preparing a discriminant (a support vector machine) using, as training samples, gene expression levels calculated from the expression levels of the target nucleic acids;

(3) measuring in vitro expression levels of the target nucleic acids in the sample from a breast cancer patient at the time of surgery or biopsy examination as in step (1); and (4) assigning, to the discriminant determined in step (2), the gene expression levels in breast cancer lesion calculated from the target nucleic acid expression levels determined in step 3, and predicting, determining, or evaluating a possibility that the breast cancer patient has a response to Trastuzumab therapy based on the results determined from the discriminant.

According to the sixth aspect, the present invention provides use of any composition above, any kit above, any DNA chip above, or a combination thereof, in a composition and a method for predicting a response to Trastuzumab therapy of a breast cancer patient, wherein the composition and method are for predicting, determining, or evaluating in vitro a possibility that the breast cancer patient has a response to Trastuzumab therapy.

2. DEFINITION

The terms used herein are as defined below.

The terms of "nucleotide," "polynucleotide," and abbreviations such as "DNA" and "RNA" are in accordance with the "Guidelines for the preparation of specification or the like that contains nucleotide sequence or amino acid sequence" (edited by the Japan Patent Office) and common usage in the art.

The term "polynucleotide" as used herein refers to a nucleic acid including either RNA or DNA. Such DNA includes any of cDNA, genomic DNA, and synthetic DNA. Such RNA includes any of total RNA, mRNA, rRNA, miRNA, siRNA, snoRNA, snRNA, non-coding RNA, and synthetic RNA. The term "polynucleotide" is used interchangeably with the term "nucleic acid."

The term "gene" as used herein refers to not only RNA or double-stranded DNA but also to single-stranded DNA such as a plus-strand (or a sense strand) or a complementary strand (or an antisense strand), such strands constituting double-stranded DNA. There are no particular limitations on the length of such a strand.

Thus, the term "gene" as used herein is intended to refer to double-stranded DNA (including human genomic DNA), single-stranded DNA (plus-strand) (including cDNA), single-stranded DNA having a sequence complementary to the plus-strand (complementary strand), a fragment thereof, or the human genome, unless otherwise specified. Such "gene" includes not only a "gene" represented by a specific nucleotide sequence (or a SEQ ID NO.) but also a "nucleic acid" encoding: RNA which has a biological function equivalent to that of RNA encoded by the gene, such as homolog or ortholog; a mutant such as polymorphism; or a derivative. Specific examples of the "nucleic acids" encoding such homolog, mutant, or derivative include "nucleic acids" each comprising a nucleotide sequence hybridizing to a sequence complementary to a nucleotide sequence represented by any of SEQ ID NOs: 1 to 23 or to a nucleotide sequence derived therefrom by substitution of u with t, under stringent conditions as described later. Functional regions of a "gene" are not limited, and examples of the gene can include an expression-control region, a coding region, exons, or introns.

The term "transcription product" as used herein refers to RNA that is synthesized by using the DNA sequence of a gene as a template. RNA is synthesized by binding RNA polymerase to a site referred to as a promoter, which is located upstream of the gene of interest, followed by binding ribonucleotides to the 3' end so as to become complementary to the nucleotide sequence of DNA. Such RNA can comprise not only the gene of interest but also a full-length sequence from a transcription initiation site to the terminus of a poly A sequence, including an expression-control region, a coding region, exons, or introns.

The term "micro RNA (miRNA)" used herein is intended to refer to non-coding RNA of 16 to 25 nucleotides, preferably 16 to 25 nucleotides, and more preferably 20 to 25 nucleotides that is associated with inhibition of mRNA translation, unless otherwise specified. Formation of miRNA includes transcription into a RNA precursor having hairpin-like structure, cleavage with a dsRNA cleavage enzyme having RNase III cleavage activity, and incorporation into a protein complex referred to as "RISC." The "miRNA" as used herein includes not only "miRNA" represented by a specific nucleotide sequence (or a SEQ ID NO.) but also a precursor of the "miRNA" (i.e., pre-miRNA or pri-miRNA), miRNA that has a biological function equivalent to that of miRNA encoded by the miRNA or the precursor, such as miRNA encoding a homolog or ortholog, a mutant such as polymorphism, or a derivative. Specifically, the "miRNA" encoding such precursor, homolog, mutant, or derivative can be identified using miRBase release 16 (mirbase.org). An example of "miRNA" has a nucleotide sequence hybridizing to a sequence complementary to a particular nucleotide sequence represented by any of SEQ ID NOs: 1 to 23 under stringent conditions as described later.

The term "probe" as used herein includes a polynucleotide and/or a polynucleotide complementary thereto, which is used for specifically detecting a RNA resulting from gene expression or a polynucleotide derived from the RNA.

The term "primer" as used herein includes a continuous polynucleotide and/or a polynucleotide complementary thereto, which specifically recognizes and amplifies RNA resulting from gene expression or a polynucleotide derived therefrom.

The complementary polynucleotide (which is a complementary strand or reverse strand) refers to a polynucleotide that has a complementary relationship between nucleotides on the basis of the base pair relationship of A:T(U) or G:C to a full-length sequence of a polynucleotide consisting of a nucleotide sequence defined by SEQ ID NO. or a nucleotide sequence derived therefrom by substitution of u with t, or a partial sequence of the full-length sequence (referred to as a "plus strand" herein for convenience). Such a complementary strand, however, is not limited to a sequence completely complementary to the nucleotide sequence of a plus strand of interest, and the complementary strand may have a complementarity relationship of the extent that allows it to hybridize to the plus strand under stringent conditions.

As used herein, the term "stringent conditions" refers to conditions that allow a probe to hybridize to a target sequence with a higher degree of detection when compared with its hybridization to other sequences (e.g., a determined value which is (a mean value of background measurements+a standard deviation of background measurements× 2) or more). Stringent conditions are dependent on the sequence of a target, and conditions vary depending on the environment in which hybridization is conducted. By controlling the stringency of hybridization and/or washing conditions, a target sequence that is 100% complementary to the probe can be identified.

As used herein, the term "mutant" in case of nucleic acid refers to a naturally-occurring mutant resulting from, for example, polymorphism or mutation, a mutant comprising a nucleotide sequence represented by any of SEQ ID NOs: 1 to 23, a nucleotide sequence derived therefrom by substitution of u with t, or a partial sequence thereof comprising a deletion, substitution, addition, or insertion of 1, 2 or 3 or more, preferably 1 or 2 nucleotides, a mutant comprising a nucleotide sequence of precursor RNA of miRNA represented by any of SEQ ID NOs: 1 to 23, a nucleotide sequence derived therefrom by substitution of u with t, or a partial sequence thereof, comprising a deletion, substitution, addition, or insertion of 1 or 2 or more, preferably 1 or several nucleotides, a mutant having approximately 90% or higher, approximately 95% or higher, approximately 97% or higher, approximately 98% or higher, or approximately 99% or higher identity with the nucleotide sequence or a partial sequence thereof, or a nucleic acid hybridizing to a polynucleotide or oligonucleotide comprising a nucleotide sequence represented by any of SEQ ID NOs: 1 to 23 or a partial sequence thereof under stringent conditions as defined above.

The term "several" as used herein means an integer of about 20, 19, 18, 17, 16, 15, 14, 13, 12, 11, 10, 9, 8, 7, 6, 5, 4, 3, or 2.

As used herein, the mutant can be prepared by a technique well known in the art, such as site-directed mutagenesis or PCR-based mutagenesis.

The term "% identity" used herein refers to a percentage of identical nucleotides relative to the total number of nucleotides (including gaps, if any exists) when two sequences are aligned so as to attain the maximal degree of consistency, and it can be determined using a protein/gene searching system such as BLAST or FASTA as mentioned above, with or without the introduction of gaps (Karlin, S. et al., 1993, Proc. Natl. Acad. Sci., U.S.A., vol. 90, pp. 5873-5877; Altschul, S. F. et al., 1990, Journal of Molecular Biology, vol. 215, pp. 403-410; Pearson, W. R. et al., 1988, Proc. Natl. Acad. Sci., U.S.A., vol. 85, pp. 2444-2448).

The term "derivative" used herein refers to a derivative comprising a modified nucleic acid, a derivative labeled with fluorophore, a derivative comprising a modified nucleotide (e.g., a nucleotide having a group such as halogen, alkyl (e.g., methyl), alkoxy (e.g., methoxy), thio, or carboxymethyl; or a nucleotide resulting from reconstitution of a base, saturation of a double bond, deamination, or substitution of oxygen molecule by sulfur molecule), peptide nucleic acid (PNA; Nielsen, P. E. et al., 1991, Science 254: 1497), or locked nucleic acid (LNA; Obika, S. et al., 1998, Tetrahedron Lett. 39: 5401), although the "derivative" is not limited thereto.

The term "composition for use in prediction, determination, detection, or diagnosis" as used herein refers to a composition that is directly or indirectly employed for diagnosing the presence or absence of or the degree of the onset or development of breast cancer, the presence or absence of or the degree of amelioration of breast cancer, or response to treatment of breast cancer, or for screening for candidate substances useful for preventing, ameliorating, or treating breast cancer. The composition comprises nucleotides, oligonucleotides, or polynucleotides that can specifically recognize and bind to genes, the expressions of which vary or fluctuate in vivo, and particularly in a mammary tissue, in association with the development of breast cancer. Such nucleotides, oligonucleotides, or polynucleotides can be effectively used as probes for detecting the aforementioned genes that are expressed in vivo, in tissues, or in cells, based on the aforementioned properties, or as primers for amplifying the genes expressed in vivo.

The term "prediction" as used herein refers to prediction, determination, evaluation, detection, or diagnosis.

As used herein, the term "sample" subjected to prediction, determination, evaluation, detection, or diagnosis refers to a tissue or biological material in which the expressions of the genes of the present invention vary upon the onset of breast cancer and the exertion of therapeutic effects on breast cancer. Specific examples include mammary tissues, vessels in the vicinity thereof, lymph nodes, organs, organs suspected of metastasis, skins, body fluids, such as blood, urine, saliva, sweat, and exudate leaking out of tissues, stools, and hairs.

The term "FFPE specimen" as used herein refers to a formalin-fixed, paraffin embedded specimen prepared by fixing a biological tissue with formalin and then embedding it in paraffin.

The term "response to Trastuzumab therapy" as used herein refers to a property that breast cancer progression is inhibited by Trastuzumab therapy. Disease progression may be detected pathologically or may be detected clinically with respect to evaluation of tumor size and patient's condition using image diagnosis. Trastuzumab therapy on a breast cancer patient may be performed with the use of Trastuzumab in combination with one or more other anticancer agents.

The term "anticancer agent" as used herein refers to a drug used in combination with Trastuzumab for drug therapy for breast cancer. Examples of anticancer agents include: alkylating agents such as cyclophosphamide and thiotepa; 5-FU-based antimetabolites such as fluorouracil, tegafur, carmofur, doxifluridine, and capecitabine; antimetabolites such as methotrexate and gemcitabine; anthracycline agents such as adriamycin, epirubicin, and pirarubicin; anthraquinone agents such as mitoxantrone; anticancer antibiotics such as mitomycin C; vinca alkaloids such as vinorelbine; taxane agents such as paclitaxel and docetaxel; topoisomerase I inhibitors such as irinotecan; antiestrogens such as tamoxifen and toremifene; aromatase inhibitors such as fadrozole, anastrozole, exemestane, and letrozole; progestagens such as medroxyprogesterone; LH-RH agonists such as goserelin and leuprorelin; platinum agents such as cisplatin and carboplatin; non-taxane microtubule dynamics inhibitors such as eribulin; and molecular-targeting agents such as lapatinib, bevacizumab, and pertuzumab.

The term "rank" as used herein refers to the rank statistics determined by the statistical test that takes into account the false-positive rate described in Rainer, B. et al., 2004, FEBS Letters, vol. 573, pp. 83-92.

The term "AUROC value" as used herein refers to an area under the receiver operating characteristic curve (the ROC curve), and it serves as the indicator for determining the accuracy of a method for prediction, determination, evaluation, detection, or diagnosis performed for classification of patients into the positive group or the negative group. In an AUROC curve, concerning the outcomes determined by the method to be evaluated, the probability that positive outcomes occur in positive patients (i.e., sensitivity) and the reciprocal numbers of the probability that negative outcomes occur in negative patients (i.e., specificity) are plotted.

According to the "leave-one-out cross-validation method (hereafter referred to as the "LOOCV method") as used herein, a single sample is removed from the data set in order to make a testing group, and this testing group and a learning group composed of the remaining samples are subjected to a certain assay to prepare a discriminant, which is evaluated using the removed single sample. This procedure is repeatedly performed on each sample in the data set, and the average of the evaluation results is regarded as indicating the overall accuracy.

The term "miR-1234 gene" or "miR-1234" used herein refers to, for example, the hsa-miR-1234 gene represented by SEQ ID NO: 1 (miRbase Accession No. MIMAT 0005589) or a homolog or ortholog thereof from another organism species. The hsa-miR-1234 gene can be obtained by the method described in Lagos-Quintana, M. et al., 2001, Science, vol. 294, pp. 853-858.

The term "miR-513a-5p gene" or "miR-513a-5p" used herein refers to, for example, the hsa-miR-513a-5p gene represented by SEQ ID NO: 2 (miRbase Accession No. MIMAT 0002877) or a homolog or ortholog thereof from another organism species. The hsa-miR-513a-5p gene can be obtained by the method described in Lagos-Quintana, M. et al., 2001, Science, vol. 294, pp. 853-858.

The term "miR-494 gene" or "miR-494" used herein refers to, for example, the hsa-miR-494 gene represented by SEQ ID NO: 3 (miRbase Accession No. MIMAT 0002816) or a homolog or ortholog thereof from another organism species. The hsa-miR-494 gene can be obtained by the method described in Lagos-Quintana, M. et al., 2001, Science, vol. 294, pp. 853-858.

The term "miR-26a gene" or "miR-26a" used herein refers to, for example, the hsa-miR-26a gene represented by SEQ ID NO: 4 (miRbase Accession No. MIMAT 0000082) or a homolog or ortholog thereof from another organism species. The hsa-miR-26a gene can be obtained by the method described in Lagos-Quintana, M. et al., 2001, Science, vol. 294, pp. 853-858.

The term "let-7a gene" or "let-7a" used herein refers to, for example, the hsa-let-7a gene represented by SEQ ID NO: 5 (miRbase Accession No. MIMAT 0000062) or a homolog or ortholog thereof from another organism species. The hsa-let-7a gene can be obtained by the method described in Lagos-Quintana, M. et al., 2001, Science, vol. 294, pp. 853-858.

The term "let-7b gene" or "let-7b" used herein refers to, for example, the hsa-let-7b gene represented by SEQ ID NO: 6 (miRbase Accession No. MIMAT 0000063) or a homolog or ortholog thereof from another organism species. The hsa-let-7b gene can be obtained by the method described in Lagos-Quintana, M. et al., 2001, Science, vol. 294, pp. 853-858.

The term "let-7g gene" or "let-7g" used herein refers to, for example, the hsa-let-7g gene represented by SEQ ID NO: 7 (miRbase Accession No. MIMAT 0000414) or a homolog or ortholog thereof from another organism species. The hsa-let-7g gene can be obtained by the method described in Lagos-Quintana, M. et al., 2001, Science, vol. 294, pp. 853-858.

The term "miR-940 gene" or "miR-940" used herein refers to, for example, the hsa-miR-940 gene represented by SEQ ID NO: 8 (miRbase Accession No. MIMAT 0004983) or a homolog or ortholog thereof from another organism species. The hsa-miR-940 gene can be obtained by the method described in Lagos-Quintana, M. et al., 2001, Science, vol. 294, pp. 853-858.

The term "miR-1470 gene" or "miR-1470" used herein refers to, for example, the hsa-miR-1470 gene represented by SEQ ID NO: 9 (miRbase Accession No. MIMAT 0007348) or a homolog or ortholog thereof from another organism species. The hsa-miR-1470 gene can be obtained by the method described in Lagos-Quintana, M. et al., 2001, Science, vol. 294, pp. 853-858.

The term "miR-125a-5p gene" or "miR-125a-5p" used herein refers to, for example, the hsa-miR-125a-5p gene represented by SEQ ID NO: 10 (miRbase Accession No. MIMAT 0000443) or a homolog or ortholog thereof from another organism species. The hsa-miR-125a-5p gene can be obtained by the method described in Lagos-Quintana, M. et al., 2001, Science, vol. 294, pp. 853-858.

The term "miR-200c gene" or "miR-200c" used herein refers to, for example, the hsa-miR-200c gene represented by SEQ ID NO: 11 (miRbase Accession No. MIMAT 0000617) or a homolog or ortholog thereof from another organism species. The hsa-miR-200c gene can be obtained by the method described in Lagos-Quintana, M. et al., 2001, Science, vol. 294, pp. 853-858.

The term "let-7e gene" or "let-7e" used herein refers to, for example, the hsa-let-7e gene represented by SEQ ID NO: 12 (miRbase Accession No. MIMAT 0000066) or a homolog or ortholog thereof from another organism species. The hsa-let-7e gene can be obtained by the method described in Lagos-Quintana, M. et al., 2001, Science, vol. 294, pp. 853-858.

The term "miR-1228 gene" or "miR-1228" used herein refers to, for example, the hsa-miR-1228 gene represented by SEQ ID NO: 13 (miRbase Accession No. MIMAT 0005583) or a homolog or ortholog thereof from another organism species. The hsa-miR-1228 gene can be obtained by the method described in Lagos-Quintana, M. et al., 2001, Science, vol. 294, pp. 853-858.

The term "let-7c gene" or "let-7c" used herein refers to, for example, the hsa-let-7c gene represented by SEQ ID NO: 14 (miRbase Accession No. MIMAT 0000064) or a homolog or ortholog thereof from another organism species. The hsa-let-7c gene can be obtained by the method described in Lagos-Quintana, M. et al., 2001, Science, vol. 294, pp. 853-858.

The term "miR-1229 gene" or "miR-1229" used herein refers to, for example, the hsa-miR-1229 gene represented by SEQ ID NO: 15 (miRbase Accession No. MIMAT 0005584) or a homolog or ortholog thereof from another organism species. The hsa-miR-1229 gene can be obtained by the method described in Lagos-Quintana, M. et al., 2001, Science, vol. 294, pp. 853-858.

The term "miR-205 gene" or "miR-205" used herein refers to, for example, the hsa-miR-205 gene represented by SEQ ID NO: 16 (miRbase Accession No. MIMAT 0000266) or a homolog or ortholog thereof from another organism species. The hsa-miR-205 gene can be obtained by the method described in Lagos-Quintana, M. et al., 2001, Science, vol. 294, pp. 853-858.

The term "miR-145 gene" or "miR-145" used herein refers to, for example, the hsa-miR-145 gene represented by SEQ ID NO: 17 (miRbase Accession No. MIMAT 0000437) or a homolog or ortholog thereof from another organism species. The hsa-miR-145 gene can be obtained by the method described in Lagos-Quintana, M. et al., 2001, Science, vol. 294, pp. 853-858.

The term "miR-181a gene" or "miR-181a" used herein refers to, for example, the hsa-miR-181a gene represented by SEQ ID NO: 18 (miRbase Accession No. MIMAT 0000256) or a homolog or ortholog thereof from another organism species. The hsa-miR-181a gene can be obtained by the method described in Lagos-Quintana, M. et al., 2001, Science, vol. 294, pp. 853-858.

The term "miR-191 gene" or "miR-191" used herein refers to, for example, the hsa-miR-191 gene represented by SEQ ID NO: 19 (miRbase Accession No. MIMAT 0000440) or a homolog or ortholog thereof from another organism species. The hsa-miR-191 gene can be obtained by the method described in Lagos-Quintana, M. et al., 2001, Science, vol. 294, pp. 853-858.

The term "miR-125b gene" or "miR-125b" used herein refers to, for example, the hsa-miR-125b gene represented by SEQ ID NO: 20 (miRbase Accession No. MIMAT 0000423) or a homolog or ortholog thereof from another organism species. The hsa-miR-125b gene can be obtained by the method described in Lagos-Quintana, M. et al., 2001, Science, vol. 294, pp. 853-858.

The term "miR-92a gene" or "miR-92a" used herein refers to, for example, the hsa-miR-92a gene represented by SEQ ID NO: 21 (miRbase Accession No. MIMAT 0000092) or a homolog or ortholog thereof from another organism species. The hsa-miR-92a gene can be obtained by the method described in Lagos-Quintana, M. et al., 2001, Science, vol. 294, pp. 853-858.

The term "let-7d gene" or "let-7d" used herein refers to, for example, the hsa-let-7d gene represented by SEQ ID NO: 22 (miRbase Accession No. MIMAT 0000065) or a homolog or ortholog thereof from another organism species. The hsa-let-7d gene can be obtained by the method described in Lagos-Quintana, M. et al., 2001, Science, vol. 294, pp. 853-858.

The term "miR-23a gene" or "miR-23a" used herein refers to, for example, the hsa-miR-23a gene represented by SEQ ID NO: 23 (miRbase Accession No. MIMAT 0000078) or a homolog or ortholog thereof from another organism species. The hsa-miR-23a gene can be obtained by the method described in Lagos-Quintana, M. et al., 2001, Science, vol. 294, pp. 853-858.

The present invention provides a composition useful for prediction (or determination, evaluation, detection, or diagnosis) of the response to Trastuzumab therapy in a breast cancer patient, a method for predicting (or determining, evaluating, detecting, or diagnosing) the response to Trastuzumab therapy of a breast cancer patient using such composition, and a kit for prediction (or determination, evaluation, detection, or diagnosis) of the response to Trastuzumab therapy in a breast cancer patient using such composition. Thus, the present invention has remarkable effects of providing a method for predicting (or determining, evaluating, detecting, or diagnosing) the response to Trastuzumab therapy of a breast cancer patient, which is carried out with high specificity and high prediction accuracy in a rapid and simple manner.

BRIEF DESCRIPTION OF THE DRAWINGS

FIG. 3 shows the results in selecting 20 genes used for prediction of the response to Trastuzumab therapy of breast cancer patients, which results are selected by the LOOCV method using SVM for selection in the procedure outlined in FIG. 1. In FIG. 3, the data indicated in rows in the table show 35 training data sets comprising 34 learning data sets and 1 testing data. The columns represent the SEQ ID NOs. of the genes used for prediction selected from the training data set. The numbers in the table each represent the priority ranking for the genes used for prediction selected from the training data set.

EMBODIMENTS FOR CARRYING OUT THE INVENTION

Figure 1:
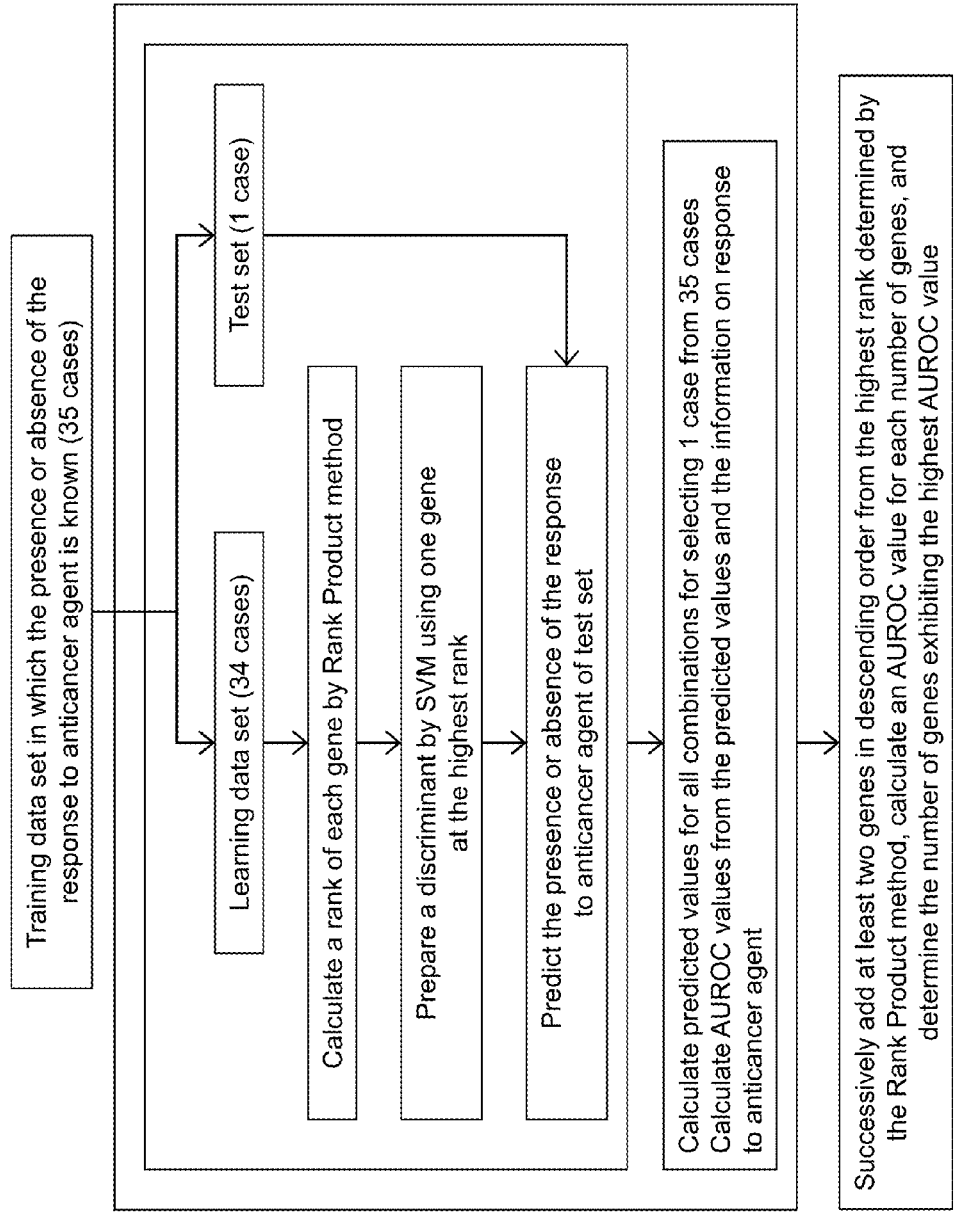
FIG. 1 shows the flow of analysis for determining the genes shown in Table 1.

Hereafter, the present invention will be described in more detail.

1. Target Nucleic Acids of Breast Cancer

Examples of target nucleic acids as markers for prediction of the response to Trastuzumab therapy in a breast cancer patient with the use of the composition and the kit for prediction of the response to Trastuzumab therapy in a breast cancer patient as defined above, include human genes each comprising a nucleotide sequence represented by any of SEQ ID NOs: 1 to 23 (i.e., miR-1234, miR-513a-5p, miR-494, miR-26a, let-7a, let-7b, let-7g, miR-940, miR-1470, miR-125a-5p, miR-200c, let-7e, miR-1228, let-7c, miR-1229, miR-205, miR-145, miR-181a, miR-191, miR-125b, miR-92a, let-7d, and miR-23a), homologs thereof, and mutants or derivatives thereof. The terms "gene," "homolog," "transcription product," "mutant," and "derivative" are as defined above. The target nucleic acids are preferably human genes, each of which comprises a nucleotide sequence represented by any of SEQ ID NOs: 1 to 23, or transcription products thereof, more preferably the transcription products (i.e., miRNA and precursor RNAs thereof (pri-miRNA and pre-miRNA)).

All the target genes described above used for prediction of the response to Trastuzumab therapy in a breast cancer patient in the present invention exhibit decreased or reduced, or increased or elevated, expression levels of genes obtained from breast cancer lesions of patients not responding to Trastuzumab therapy, compared with those obtained from breast cancer patients responding to Trastuzumab therapy (see Table 1 in Examples later).

The 1st target nucleic acid is the miR-1234 gene, a homolog thereof, a transcription product, or a mutant or derivative thereof. Up to the present, there have been no reports that expression of the miR-1234 gene or a transcription product thereof could function as a prediction marker for the response to Trastuzumab therapy in a breast cancer patient.

The 2nd target nucleic acid is the miR-513a-5p gene, a homolog thereof, a transcription product thereof, or a mutant or derivative thereof. Up to the present, there have been no reports that expression of the miR-513a-5p gene or a transcription product thereof could function as a prediction marker for the response to Trastuzumab therapy in a breast cancer patient.

The 3rd target nucleic acid is the miR-494 gene, a homolog thereof, a transcription product thereof, or a mutant or derivative thereof. Up to the present, there have been no reports that expression of the miR-494 gene or a transcription product thereof could function as a prediction marker for the response to Trastuzumab therapy in a breast cancer patient.

The 4th target nucleic acid is the miR-26a gene, a homolog thereof, a transcription product thereof, or a mutant or derivative thereof. Up to the present, there have been no reports that expression of the miR-26a gene or a transcription product thereof could function as a prediction marker for the response to Trastuzumab therapy in a breast cancer patient.

The 5th target nucleic acid is the let-7a gene, a homolog thereof, a transcription product thereof, or a mutant or derivative thereof. While the expression level of the let-7a gene or a transcription thereof has been known to lower in a breast cancer patient (Patent Document 1), there have been no reports that such expression could function as a prediction marker for the response to Trastuzumab therapy in a breast cancer patient.

The 6th target nucleic acid is the let-7b gene, a homolog thereof, a transcription product thereof, or a mutant or derivative thereof. While the expression level of the let-7b gene or a transcription thereof has been known to lower in a breast cancer patient (Patent Document 1), there have been no reports that such expression could function as a prediction marker for the response to Trastuzumab therapy in a breast cancer patient.

The 7th target nucleic acid is the let-7g gene, a homolog thereof, a transcription product thereof, or a mutant or derivative thereof. Up to the present, there have been no reports that expression of the let-7g gene or a transcription product thereof could function as a prediction marker for the response to Trastuzumab therapy in a breast cancer patient.

The 8th target nucleic acid is the miR-940 gene, a homolog thereof, a transcription product thereof, or a mutant or derivative thereof. Up to the present, there have been no reports that expression of the miR-940 gene or a transcription product thereof could function as a prediction marker for the response to Trastuzumab therapy in a breast cancer patient.

The 9th target nucleic acid is the miR-1470 gene, a homolog thereof, a transcription product thereof, or a mutant or derivative thereof. Up to the present, there have been no reports that expression of the miR-1470 gene or a transcription product thereof could function as a prediction marker for the response to Trastuzumab therapy in a breast cancer patient.

The 10th target nucleic acid is the miR-125a-5p gene, a homolog thereof, a transcription product thereof, or a mutant or derivative thereof. While the increased expression level of the miR-125a gene or a transcription thereof has been known to result in the lowered expression level of Her2 protein that is targeted by Trastuzumab (Non-Patent Document 5), there have been no reports that the expression level of the miR-125a gene enables prediction of the response to Trastuzumab therapy in a patient with Her2-positive breast cancer.

The 11th target nucleic acid is the miR-200c gene, a homolog thereof, a transcription product thereof, or a mutant or derivative thereof. While the expression level of the miR-200c gene or a transcription thereof has been known to lower in a breast cancer patient (Patent Document 2), there have been no reports that such expression could function as a prediction marker for the response to Trastuzumab therapy in a breast cancer patient.

The 12th target nucleic acid is the let-7e gene, a homolog thereof, a transcription product thereof, or a mutant or derivative thereof. Up to the present, there have been no reports that expression of the let-7e gene or a transcription product thereof could function as a prediction marker for the response to Trastuzumab therapy in a breast cancer patient.

The 13th target nucleic acid is the miR-1228 gene, a homolog thereof, a transcription product thereof, or a mutant or derivative thereof. Up to the present, there have been no reports that expression of the miR-1228 gene or a transcription product thereof could function as a prediction marker for the response to Trastuzumab therapy in a breast cancer patient.

The 14th target nucleic acid is the let-7c gene, a homolog thereof, a transcription product thereof, or a mutant or derivative thereof. Up to the present, there have been no reports that expression of the let-7c gene or a transcription product thereof could function as a prediction marker for the response to Trastuzumab therapy in a breast cancer patient.

The 15th target nucleic acid is the miR-1229 gene, a homolog thereof, a transcription product thereof, or a mutant or derivative thereof. Up to the present, there have been no reports that expression of the miR-1229 gene or a transcription product thereof could function as a prediction marker for the response to Trastuzumab therapy in a breast cancer patient.

The 16th target nucleic acid is the miR-205 gene, a homolog thereof, a transcription product thereof, or a mutant or derivative thereof. Up to the present, there have been no reports that expression of the miR-205 gene or a transcription product thereof could function as a prediction marker for the response to Trastuzumab therapy in a breast cancer patient.

The 17th target nucleic acid is the miR-145 gene, a homolog thereof, a transcription product thereof, or a mutant or derivative thereof. While the expression level of the miR-145 gene or a transcription thereof has been known to lower in a breast cancer patient (Patent Document 3), there have been no reports that such expression could function as a prediction marker for the response to Trastuzumab therapy in a breast cancer patient.

The 18th target nucleic acid is the miR-181a gene, a homolog thereof, a transcription product thereof, or a mutant or derivative thereof. Up to the present, there have been no reports that expression of the miR-181a gene or a transcription product thereof could function as a prediction marker for the response to Trastuzumab therapy in a breast cancer patient.

The 19th target nucleic acid is the miR-191 gene, a homolog thereof, a transcription product thereof, or a mutant or derivative thereof. Up to the present, there have been no reports that expression of the miR-191 gene or a transcription product thereof could function as a prediction marker for the response to Trastuzumab therapy in a breast cancer patient.

The 20th target nucleic acid is the miR-125b gene, a homolog thereof, a transcription product thereof, or a mutant or derivative thereof. While the increased expression level of the miR-125b gene or a transcription thereof has been known to result in the lowered expression level of Her2 protein that is targeted by Trastuzumab (Non-Patent Document 5), there have been no reports that the expression level of miR-125b enables prediction of the response to Trastuzumab therapy in a patient with Her2-positive breast cancer.

The 21st target nucleic acid is the miR-92a gene, a homolog thereof, a transcription product thereof, or a mutant or derivative thereof. Up to the present, there have been no reports that expression of the miR-92a gene or a transcription product thereof could function as a prediction marker for the response to Trastuzumab therapy in a breast cancer patient.

The 22nd target nucleic acid is the let-7d gene, a homolog thereof, a transcription product thereof, or a mutant or derivative thereof. Up to the present, there have been no reports that expression of the let-7d gene or a transcription product thereof could function as a prediction marker for the response to Trastuzumab therapy in a breast cancer patient.

The 23rd target nucleic acid is the miR-23a gene, a homolog thereof, a transcription product thereof, or a mutant or derivative thereof. Up to the present, there have been no reports that expression of the miR-23a gene or a transcription product thereof could function as a prediction marker for the response to Trastuzumab therapy in a breast cancer patient.

2. Composition for Use in Prediction of Response to Trastuzumab Therapy in Breast Cancer Patient According to the present invention, the nucleic acid composition that can be used for prediction of the response to Trastuzumab therapy in a breast cancer patient enables qualitative and/or quantitative assays concerning the presence, the gene expression levels, or the existing amounts of target nucleic acids; that is, human-derived miR-1234, miR-513a-5p, miR-494, miR-26a, let-7a, let-7b, let-7g, miR-940, miR-1470, miR-125a-5p, miR-200c, let-7e, miR-1228, let-7c, miR-1229, miR-205, miR-145, miR-181a, miR-191, miR-125b, miR-92a, let-7d, and miR-23a, homologs thereof, and mutants or derivatives thereof.

All the target nucleic acids described above exhibit decreased or reduced, or increased or elevated, expression levels of genes obtained from breast cancer tissues of breast cancer patients with lower response to Trastuzumab, compared with patients having higher response to Trastuzumab. Thus, the composition of the present invention can be effectively used for measurement of target nucleic acid expression levels in breast cancer tissues and for comparison of such levels in breast cancer tissues obtained from patients exhibiting high response to Trastuzumab therapy with those in breast cancer tissues obtained from patients exhibiting low response to Trastuzumab therapy.

The composition that can be used in the present invention comprises a combination of two or more polynucleotides selected from the group consisting of: polynucleotides each comprising a nucleotide sequence represented by any of SEQ ID NOs: 1 to 23, or a nucleotide sequence derived therefrom by substitution of u with t, from a sample obtained from a patient suffered from breast cancer, and polynucleotides complementary thereto; polynucleotides each hybridizing under stringent conditions to DNA comprising a nucleotide sequence complementary to the nucleotide sequence, and polynucleotides complementary thereto; and polynucleotides comprising at least 16, preferably 21-24 continuous nucleotides in any of the nucleotide sequences of the aforementioned polynucleotides. Such polynucleotides can be used as probes or primers for detection of target nucleic acids (i.e., the prediction markers as mentioned above).

Specifically, the composition of the present invention may comprise two or more polynucleotides selected from the group consisting of polynucleotides as set forth below, mutants thereof, derivatives thereof, or fragments thereof:

(1) polynucleotides each consisting of a nucleotide sequence represented by any of SEQ ID NOs: 1 to 23 or a nucleotide sequence derived therefrom by substitution of u with t, mutants thereof, derivatives thereof, or fragments thereof comprising at least 16 continuous nucleotides;

(2) polynucleotides each comprising a nucleotide sequence represented by any of SEQ ID NOs: 1 to 23 or a nucleotide sequence derived therefrom by substitution of u with t;

(3) polynucleotides each consisting of a nucleotide sequence represented by any of SEQ ID NOs: 1 to 9, 11 to 19, and 21 to 23 or a nucleotide sequence derived therefrom by substitution of u with t, mutants thereof, derivatives thereof, or fragments thereof comprising at least 16 continuous nucleotides;

(4) polynucleotides each comprising a nucleotide sequence represented by any of SEQ ID NOs: 1 to 9, 11 to 19, and 21 to 23 or a nucleotide sequence derived therefrom by substitution of u with t;

(5) polynucleotides each consisting of an nucleotide sequence complementary to a nucleotide sequence represented by any of SEQ ID NOs: 1 to 9, 11 to 19, and 21 to 23 or to a nucleotide sequence derived therefrom by substitution of u with t, mutants thereof, derivatives thereof, or fragments thereof comprising at least 16 continuous nucleotides;

(6) polynucleotides each comprising a nucleotide sequence complementary to a nucleotide sequence represented by any of SEQ ID NOs: 1 to 9, 11 to 19, and 21 to 23 or to a nucleotide sequence derived therefrom by substitution of u with t;

(7) polynucleotides each hybridizing under stringent conditions to a polynucleotide consisting of a nucleotide sequence complementary to a nucleotide sequence derived from a nucleotide sequence represented by any of SEQ ID NOs: 1 to 9, 11 to 19, and 21 to 23 by substitution of u with t, or fragments thereof comprising at least 16 continuous nucleotides;

(8) polynucleotides each consisting of the nucleotide sequence represented by any of SEQ ID NOs: 10 and 20 or a nucleotide sequence derived therefrom by substitution of u with t, mutants thereof, derivatives thereof, or fragments thereof comprising at least 16 continuous nucleotides;

(9) polynucleotides each comprising the nucleotide sequence represented by any of SEQ ID NOs: 10 and 20 or a nucleotide sequence derived therefrom by substitution of u with t;

(10) polynucleotides each consisting of a nucleotide sequence complementary to the nucleotide sequence represented by any of SEQ ID NOs: 10 and 20 or to a nucleotide sequence derived therefrom by substitution of u with t, mutants thereof, derivatives thereof, or fragments thereof comprising at least 16 continuous nucleotides;

(11) polynucleotides each comprising a nucleotide sequence complementary to the nucleotide sequence represented by any of SEQ ID NOs: 10 and 20 or to a nucleotide sequence derived therefrom by substitution of u with t; and

(12) polynucleotides each hybridizing under stringent conditions to a polynucleotide consisting of a nucleotide sequence complementary to a nucleotide sequence derived from the nucleotide sequence represented by any of SEQ ID NOs: 10 and 20 by substitution of u with t, or fragments thereof comprising at least 16 continuous nucleotides.

Fragments of the polynucleotides (1) to (12) above can comprise nucleotide numbers ranging, for example, from 16 continuous nucleotides to all continuous nucleotides of each sequence, such as 16-24, 18-24, or 21-24 nucleotides, in the nucleotide sequence of each polynucleotide, mutant, or derivative, although the number of nucleotides is not limited thereto.

The polynucleotides or fragments thereof as used in the present invention may be DNA or RNA.

Polynucleotides in the compositions of the present invention can be prepared by general techniques such as recombinant DNA technology, PCR, or a method using automatic DNA/RNA synthesizer.

Recombinant DNA technology, site-directed mutagenesis, and PCR can employ the techniques as disclosed in, for example, Ausubel. et al., Current Protocols in Molecular Biology, John Willey & Sons, U.S.A., 1993; or Sambrook et al., Molecular Cloning: A Laboratory Manual, Cold Spring Harbor Laboratory Press, U.S.A., 1989.

Human-derived miR-1234, miR-513a-5p, miR-494, miR-26a, let-7a, let-7b, let-7g, miR-940, miR-1470, miR-125a-5p, miR-200c, let-7e, miR-1228, let-7c, miR-1229, miR-205, miR-145, miR-181a, miR-191, miR-125b, miR-92a, let-7d, and miR-23a genes are known, and the methods for obtaining the same are also known as described above. Thus, these genes can be cloned in order to prepare polynucleotides as the compositions of the present invention.

Polynucleotides constituting the composition of the present invention may be chemically synthesized using an automatic DNA synthesizer. Such synthesis is generally carried out by the phosphoramidite method, which enables the automatic synthesis of a single-stranded DNA for full-length microRNA. The automatic DNA synthesizer is commercially available from, for example, Polygen or Life Technologies.

Also, the polynucleotides of the present invention can be prepared by cDNA cloning. The cDNA cloning can be carried out using, for example, the Wako microRNA Cloning Kit (Wako Pure Chemical Industries, Ltd.).

3. Kit for Prediction of the Response to Trastuzumab Therapy in Breast Cancer Patient The present invention also provides a kit for prediction of the response to Trastuzumab therapy in a breast cancer patient comprising two or more polynucleotides of the same polynucleotides as those contained in the composition of the present invention, mutants thereof, and/or fragments thereof.

The kit of the present invention comprises two or more polynucleotides selected from the polynucleotides described in §2 above, mutants thereof, derivatives thereof, and/or fragments thereof. The mutants and the derivatives as defined above may be used herein.

The kit of the present invention can comprise two or more polynucleotides of: polynucleotides each comprising a nucleotide sequence represented by any of SEQ ID NOs: 1 to 9, 11 to 19, and 21 to 23 or a nucleotide sequence derived therefrom by substitution of u with t; polynucleotides each comprising a complementary sequence thereof; polynucleotides each hybridizing under stringent conditions to the polynucleotide above; or fragments such polynucleotides; mutants such polynucleotides; or derivatives of such polynucleotides.

The kit of the present invention can further comprise one or more polynucleotides of: polynucleotides each comprising a nucleotide sequence represented by any of SEQ ID NOs: 10 and 20 or a nucleotide sequence derived therefrom by substitution of u with t; polynucleotides each comprising a complementary sequence thereof; polynucleotides each hybridizing under stringent conditions to the polynucleotide above; or fragments of such polynucleotides.

Polynucleotide fragments that can be contained in the kit of the present invention are, for example, two or more DNAs selected from the group consisting of (1) and (2) below:

(1) DNA comprising at least 16 continuous nucleotides in a nucleotide sequence derived from a nucleotide sequence represented by any of SEQ ID NOs: 1 to 9, 11 to 19, and 21 to 23 by substitution of u with t, or in a sequence complementary thereto; and (2) additional DNA comprising at least 16 continuous nucleotides in a nucleotide sequence derived from the nucleotide sequence represented by SEQ ID NO: 10 or 20 by substitution of u with t or in a sequence complementary thereto, in addition to DNA comprising at least 16 continuous nucleotides in a nucleotide sequence derived from a nucleotide sequence represented by any of SEQ ID NOs: 1 to 9, 11 to 19, and 21 to 23 by substitution of u with t or in a sequence complementary thereto.

According to a preferred embodiment, the polynucleotide is a polynucleotide consisting of a nucleotide sequence represented by any of SEQ ID NOs: 1 to 9, 11 to 19, and 21 to 23 or a nucleotide sequence derived therefrom by substitution of u with t, a polynucleotide consisting of a sequence complementary thereto; a polynucleotide hybridizing under stringent conditions to the polynucleotide above, or a fragment thereof comprising at least 16, preferably 21-24 continuous nucleotides.

According to another preferred embodiment, the kit of the present invention can further comprise a polynucleotide consisting of the nucleotide sequence represented by SEQ ID NO: 10 or 20 or a nucleotide sequence derived therefrom by substitution of u with t, a polynucleotide consisting of a complementary sequence thereof, a polynucleotide hybridizing under stringent conditions to the polynucleotide above, or a fragment thereof comprising at least 16, preferably 21-24 continuous nucleotides, in addition to the above-described polynucleotides.

The present invention also provides a kit for prediction of the response to Trastuzumab therapy in a breast cancer patient comprising measuring expression levels of two or more genes in the breast cancer tissue of a breast cancer patient as calculated from the gene expression levels of the same polynucleotides as those contained in the composition of the present invention, mutants thereof, and/or fragments thereof.

According to the present invention, the size of a polynucleotide fragment is a nucleotide number ranging, for example, from 16 continuous nucleotides to all continuous nucleotides of each sequence, such as 16-24, 18-24, or 21-24 nucleotides in the nucleotide sequence of each polynucleotide above, each mutant thereof above, or each derivative thereof above.

In addition to the polynucleotides according to the present invention described above, mutants thereof, or fragments thereof, the kit of the present invention can comprise polynucleotides that are known or will be found in the future and enable prediction of the response to Trastuzumab therapy in a breast cancer patient.

The polynucleotides, mutants thereof, or fragments thereof contained in the kit of the present invention are packaged in different containers separately or in any combination.

4. DNA Chip

The present invention further provides a DNA chip for prediction of the response to Trastuzumab therapy in a breast cancer patient comprising the same polynucleotides as those contained in the composition and/or the kit according to the present invention (or polynucleotides described in §2. "Composition" and/or §3 "Kit"), mutants thereof, fragments thereof, or combinations thereof.

The substrate of the DNA chip is not particularly limited, provided that the substrate is able to comprise DNAs immobilized thereon. Examples of such a substrate include a glass slide, a silicon chip, a polymer chip, and a nylon membrane. Such substrate may be subjected to surface treatment, such as poly-L-lysine coating or introduction of a functional group such as an amino group or carboxyl group.

DNAs can be immobilized on a substrate by any general technique without particular limitation. Examples of such technique include a method of spotting DNA using a high-density dispenser (i.e., a spotter or arrayer), a method of spraying DNA on a substrate using an apparatus (e.g., inkjet) that jets fine droplets from a nozzle via a piezoelectric element or the like, and a method of synthesizing nucleotides successively on a substrate. When the high-density dispenser is used, for example, different gene solutions are first placed into each well of a multiwell plate, and the solutions are taken out of the plate using a pin (i.e., needle) and successively spotted on the substrate. According to the inkjet technique, genes are jetted from a nozzle and arrayed on the substrate at a high speed. For DNA synthesis on the substrate, nucleotides on the substrate are protected with a functional group that can be removed from the substrate with light or heat, and light or heat is selectively applied to a nucleotide alone at a specific position using a mask, thereby removing the protective functional group. Thereafter, nucleotides are added to a reaction solution, followed by coupling the nucleotides with the nucleotides on the substrate, and this step is repeated.

Polynucleotides to be immobilized are all the polynucleotides of the present invention as described above.

Examples of such polynucleotides can include two or more polynucleotides selected from the group consisting of the polynucleotides described below, mutants thereof, derivatives thereof, or fragments thereof:

(1) polynucleotides each consisting of a nucleotide sequence represented by any of SEQ ID NOs: 1 to 23 or a nucleotide sequence derived therefrom by substitution of u with t, mutants thereof, derivatives thereof, or fragments thereof comprising at least 16 continuous nucleotides;

(2) polynucleotides each comprising a nucleotide sequence represented by any of SEQ ID NOs: 1 to 23 or a nucleotide sequence derived therefrom by substitution of u with t;

(3) polynucleotides each consisting of a nucleotide sequence represented by any of SEQ ID NOs: 1 to 9, 11 to 19, and 21 to 23 or a nucleotide sequence derived therefrom by substitution of u with t, mutants thereof, derivatives thereof, or fragments thereof comprising at least 16 continuous nucleotides;

(4) polynucleotides comprising a nucleotide sequence represented by any of SEQ ID NOs: 1 to 9, 11 to 19, and 21 to 23 or a nucleotide sequence derived therefrom by substitution of u with t;

(5) polynucleotides each consisting of a nucleotide sequence complementary to a nucleotide sequence represented by any of SEQ ID NOs: 1 to 9, 11 to 19, and 21 to 23 or a nucleotide sequence derived therefrom by substitution of u with t, mutants thereof, derivatives thereof, or fragments thereof comprising at least 16 continuous nucleotides;

(6) polynucleotides each comprising a nucleotide sequence complementary to a nucleotide sequence represented by any of SEQ ID NOs: 1 to 9, 11 to 19, and 21 to 23 or to a nucleotide sequence derived therefrom by substitution of u with t; and (7) polynucleotides each hybridizing under stringent conditions to any of polynucleotides (3) to (6) above, or fragments thereof comprising at least 16 continuous nucleotides.

(8) each consisting of the nucleotide sequence represented by any of SEQ ID NOs: 10 and 20 or a nucleotide sequence derived therefrom by substitution of u with t, mutants thereof, derivatives thereof, or fragments thereof comprising at least 16 continuous nucleotides;

(9) polynucleotides each comprising the nucleotide sequence represented by any of SEQ ID NOs: 10 and 20 or a nucleotide sequence derived therefrom by substitution of u with t;

(10) polynucleotides each consisting of a nucleotide sequence complementary to the nucleotide sequence represented by any of SEQ ID NOs: 10 and 20 or to a nucleotide sequence derived therefrom by substitution of u with t, mutants thereof, derivatives thereof, or fragments thereof comprising at least 16 continuous nucleotides;

(11) polynucleotides each comprising a nucleotide sequence complementary to the nucleotide sequence represented by any of SEQ ID NOs: 10 and 20 or to a nucleotide sequence derived therefrom by substitution of u with t; and

(12) polynucleotides each hybridizing under stringent conditions to any of polynucleotides (8) to (11) above or fragments thereof comprising at least 16 continuous nucleotides.

According to the present invention, the size of a polynucleotide fragment is a nucleotide number ranging, for example, from 16 continuous nucleotides to all continuous nucleotides of each sequence, such as 16-24, 18-24, or 21-24 nucleotides in the nucleotide sequence of each polynucleotide above, each mutant thereof above, or each derivative thereof above.

According to a preferred embodiment, the DNA chip of the present invention can comprise two to all polynucleotides of the polynucleotides each comprising a nucleotide sequence represented by any of SEQ ID NOs: 1 to 23, or a nucleotide sequence derived therefrom by substitution of u with t, or complementary sequences thereof.

According to the present invention, the polynucleotides to be immobilized may be genomic DNA, cDNA, RNA, synthetic DNA, or synthetic RNA, and they may be single-stranded or double-stranded. Synthetic DNA and synthetic RNA include modified nucleic acids as described in the definition of "derivative" above.

Examples of DNA chips that can detect or determine the expression levels of the target genes, RNAs, or cDNAs include the 3D-Gene® Human miRNA Oligo chip (Toray Industries, Inc.), the Human miRNA Microarray Kit (V2) (Agilent), and the miRCURY LNA® microRNA ARRAY (EXIQON).

DNA chips can be prepared by, for example, a method wherein probes that have been prepared in advance are immobilized on the surface of a solid-phase subject. In this method, polynucleotides into which functional groups have been introduced are synthesized, and oligonucleotides or polynucleotides are spotted onto the surface of a surface-treated solid-phase substrate, so that covalent bonds are formed (e.g., J. B. Lamture et al., Nucleic. Acids. Research, 1994, vol. 22, pp. 2121-2125; and Z. Guo et al., Nucleic. Acids. Research, 1994, vol. 22, pp. 5456-5465). In general, the polynucleotides are covalently bound to the surface-treated solid-phase substrate via a spacer or crosslinker. A method wherein fine pieces of polyacrylamide gel are aligned on the glass surface and synthetic polynucleotides are covalently bound thereto, is also known (G. Yershov et al., Proc. Natl. Acad. Sci., U.S.A., 1996, vol. 94, p. 4913). Also, a method in which a microelectrode array is prepared on a silica microarray, a permeable layer of streptavidin-containing agarose is formed on the electrode to prepare a reaction site, this site is positively charged to immobilize the biotinylated polynucleotides thereon, and the charge at the site is regulated so as to enable hybridization under stringent conditions at a high speed, is also known (R. G. Sosnowski et al., Proc. Natl. Acad. Sci., U.S.A., 1997, vol. 94, pp. 1119-1123).

When the DNA chip analysis is employed, the DNA chip comprising the diagnostic composition of the present invention as (single-stranded or double-stranded) DNA probes attached to a substrate is used. The substrate comprising genes immobilized thereon is generally called a DNA chip or DNA array. The DNA chip includes DNA macroarray and DNA microarray. As used herein, the term "DNA chip" is also intended to refer to such DNA array.

5. Method for Detecting the Prediction of the Response to Trastuzumab Therapy of Breast Cancer Patients The present invention provides a method for predicting in vitro a response to Trastuzumab therapy of a breast cancer patient using the composition, the kit, or the DNA chip of the present invention alone or in combination, wherein the method comprises: analyzing gene expression levels in samples obtained from breast cancer patients at the time of surgery or biopsy examination (i.e., breast cancer tissues) with the use of the DNA chip composed of the diagnostic composition; comparing gene expression levels in samples obtained from breast cancer patients responding to Trastuzumab therapy with gene expression levels in samples obtained from breast cancer patients not responding to Trastuzumab therapy; and, when expression levels of the genes obtained from the breast cancer tissue, which levels are calculated from the expression levels of the target nucleic acids in the samples, are decreased or reduced, or increased or elevated, predicting the response to Trastuzumab therapy of a breast cancer patient, wherein the target nucleic acids can be detected using polynucleotides, mutants thereof, or fragments thereof, contained in the composition, kit, or DNA chip.

The present invention also provides the use of the composition of the present invention or the kit or DNA chip constituted by the composition to measure gene expression levels, for in vitro predicting a possibility showing the response to Trastuzumab therapy in a breast cancer patient.

The method of the present invention comprises the use of the composition, kit, or DNA chip comprising the polynucleotides, mutants thereof, or fragments thereof of the present invention alone or in any possible combination, as described above.

In the present invention, the polynucleotides, mutants thereof, or fragments thereof, which are contained in the composition, kit, or DNA chip of the present invention, can be used as primers or probes in prediction of the response to Trastuzumab therapy of a breast cancer patient. When used as primers, for example, TaqMan® MicroRNA Assays (Life Technologies) can be used, although primers are not limited thereto.

The polynucleotides, mutants thereof, or fragments thereof, which are contained in the composition or kit of the present invention, can be used as primers or probes in accordance with conventional techniques in known methods that specifically detect certain genes (e.g., Northern blotting, Southern blotting, RT-PCR, in situ hybridization, or Southern hybridization). Samples to be measured are collected from a breast cancer tissue sample obtained from a breast cancer patient at the time of surgery or biopsy examination, depending on types of detection methods to be employed. The breast cancer tissue sample obtained from a breast cancer patient may be maintained in a fresh state or a frozen state, or may be fixed with formalin. As a formalin solution, commercially available formalin (formaldehyde concentration: 37%) diluted with water may be used. The pH of the solution diluted with water may be adjusted to neutral with calcium carbonate, magnesium carbonate, or the like, or by dilution with a phosphate buffer, and the resultant may be preferably used. Alternatively, a formalin solution adjusted to a given concentration after removal of offensive or irritant odor may be used. Formaldehyde content in the formalin solution is preferably 1% to 30%, and more preferably 2% to 20%. An FFPE specimen that contains a formalin-fixed tissue embedded in paraffin may be used as a sample. Total RNA prepared from such sample/specimen in accordance with a conventional technique may be used, and a variety of polynucleotides containing cDNA prepared from such RNA may be used.

Specimens may be removed from patients before or after the initiation of treatment with Trastuzumab alone or in combination with anticancer agent, desirably before the initiation of treatment with Trastuzumab alone or in combination with anticancer agent.

Also, the expression levels of the nucleic acids, such as genes, RNAs, or cDNAs, of the present invention in a removed sample can be detected or quantified using the DNA chip. In this case, the composition or kit of the present invention can be used as probes for DNA chip. Such a DNA chip may be hybridized to labeled DNAs or RNAs prepared from RNAs collected from a sample, and a complex of probe and labeled DNA or RNA formed by the hybridization may be detected using the label of the labeled DNA or RNA as an indicator, thereby evaluating the presence or absence of the expression of genes using the composition of the present invention for prediction of the response to Trastuzumab therapy in a breast cancer patient, or evaluating the expression levels of genes (or gene expression levels) in a sample. In the method of the present invention, a DNA chip is preferably usable and enables the simultaneous evaluation of the presence or absence of the expression of a plurality of genes or the simultaneous evaluation of expression levels of the genes in a single biological sample.

The composition, kit, or DNA chip of the present invention is useful for prediction of the response to Trastuzumab therapy in a breast cancer patient. Specifically, the prediction can be made in the following manner. That is, the prediction of the response to Trastuzumab therapy in a breast cancer patient using the composition, kit or DNA chip can be performed by using a breast cancer tissue, which is a sample removed at the time of surgery or biopsy examination, from a patient with breast cancer to measure expression levels of the genes for the diagnostic composition in the sample, and comparing the expression levels of the genes in the sample from the breast cancer patient exhibiting the response to Trastuzumab therapy, with expression levels of the same genes in samples from breast cancer patients exhibiting no response to Trastuzumab therapy, thereby determining through the comparison whether the gene expression levels in breast cancer tissue calculated from target nucleic acids in the sample is decreased or reduced, or increased or elevated. In this case, a difference in gene expression level includes the presence or absence of the expression of the genes for the diagnostic composition.

The method for predicting the response to Trastuzumab therapy of a breast cancer patient using the composition, kit, or DNA chip of the present invention comprises: using all or part of samples removed from breast cancer patients at the time of biopsy examination or breast cancer patients' tissue samples excised by surgery, to measure gene expression levels in the samples using a polynucleotide or polynucleotides selected from among the polynucleotides of the diagnostic composition, mutants thereof, or fragments thereof; and comparing the expression levels of the genes in the sample from the breast cancer patient exhibiting the response to Trastuzumab therapy, with expression levels of the same genes in samples from breast cancer patients exhibiting no response to Trastuzumab therapy, thereby determining through the comparison whether the gene expression levels in breast cancer tissue calculated from target nucleic acids in the sample is decreased or reduced, or increased or elevated, so that the response to Trastuzumab therapy in breast cancer patients is predicted.

The method of the present invention can comprise, for example, the following steps (a), (b), and (c) of (a) bringing a sample from a breast cancer patient into contact with polynucleotides of the composition, kit, or DNA chip of the present invention;

(b) measuring expression levels of target nucleic acids in the sample using the polynucleotides as the probes; and (c) predicting a breast cancer patient's response to Trastuzumab therapy based on the results obtained in step (b).

Examples of samples or specimens used in the method of the present invention include samples prepared from breast cancer patients' samples, such as mammary tissues, peripheral tissues thereof, or tissues suspected of having breast cancer. Specifically, an RNA-containing sample prepared from such tissue, or a sample containing polynucleotides further prepared therefrom, can be prepared by removing all or part of samples from the breast cancer patient by biopsy examination or collecting a sample from the tissue excised by surgery.

The term "patient" as used herein refers to a mammal suffered from breast cancer or strongly suspected of having breast cancer. Examples of the patient include, but are not limited to, humans, monkeys, dogs, mice, and rats, preferably humans.

In the method of the present invention, the above-mentioned steps may be varied depending on the types of biological samples used as analytes for measurement.

When RNA is used as the analyte, the prediction of a breast cancer patient's response to Trastuzumab therapy can comprise, for example, the following steps (a), (b), and (c) of:

(a) allowing RNAs prepared from a biological sample of a breast cancer patient or complementary polynucleotides (cDNAs) transcribed therefrom to bind to polynucleotides contained in the composition, kit, or DNA chip of the present invention;

(b) measuring the RNAs prepared from the biological sample bound to the polynucleotides or complementary polynucleotides transcribed from the RNAs using the above polynucleotides as probes; and (c) predicting whether or not a breast cancer patient responds to Trastuzumab therapy based on the results obtained in step (b).

In order to predict a breast cancer patient's response to Trastuzumab therapy using the present invention, for example, various hybridization techniques can be employed. Examples of the hybridization techniques that can be employed include Northern blotting, Southern blotting, PCR, RT-PCR, DNA chip analysis, in situ hybridization, and Southern hybridization.

When Northern blotting is employed, the diagnostic composition of the present invention can be used as probes to detect the presence or absence of RNA gene expression and measure the expression levels thereof. Specifically, the diagnostic composition (a complementary strand) used for prediction of prognosis in the present invention is labeled with a radioisotope (e.g., $^{32}P$, $^{33}P$, or $^{35}S$) or a fluorophore (e.g., a cyan-, rhodamine-, or fluorescamine-based fluorophore), the resultant is hybridized to the RNA in a sample obtained from a subject that has been transferred onto a nylon membrane or the like in accordance with conventional techniques, and the resulting double strand of the diagnostic composition (i.e., DNA) and the RNA can be detected and measured by detecting a signal derived from the label (a radioisotope or fluorophore) of the diagnostic composition using a radio detector (e.g., BAS-1800 II, Fuji Photo Film) or a fluorescent detector (STORM 860, GE Healthcare).

When quantitative RT-PCR is employed, polynucleotides in the diagnostic composition of the present invention can be used as primers to detect and measure the presence or absence of the gene expression in RNA or the expression level thereof. Specifically, cDNA is prepared from RNA in the sample obtained from a subject in accordance with conventional techniques, a pair of primers prepared from the composition of the present invention (i.e., a forward strand and a reverse strand, both binding to the cDNA) is hybridized to the cDNA to perform the PCR method using the cDNA as a template in accordance with conventional techniques, thereby amplifying a target gene region, and the resulting double-stranded DNA is detected. Double-stranded DNA can be detected by a method wherein PCR is carried out using primers that have been labeled with a radioisotope or fluorophore in advance, a method wherein the PCR product is electrophoresed on agarose gel and double-stranded DNA is detected by staining the same with ethidium bromide or the like, or a method wherein the resulting double-stranded DNA is transferred to a nylon membrane or the like in accordance with conventional techniques and the resultant is subjected to hybridization to polynucleotides in the labeled diagnostic composition as probes to detect a substance of interest.

Hybridization conditions are not particularly limited. For example, hybridization may be carried out in a solution containing SSC and a surfactant at 30° C. to 60° C. for 1 to 24 hours, wherein "1×SSC" refers to an aqueous solution containing 150 mM sodium chloride and 15 mM sodium citrate (pH 7.2), and examples of the surfactant includes SDS, Triton, and Tween. More preferably, the hybridization conditions comprise 3-4×SSC and 0.1-0.5% SDS. After hybridization, washing is continuously carried out with a solution of 0.5×SSC and 0.1% SDS at 30° C., a solution of 0.2×SSC and 0.1% SDS at 30° C., and a solution of 0.05×SSC at 30° C., for example. Preferably, a complementary strand remains hybridized to the target forward strand even if it is washed under such conditions. Specific examples of such complementary strand include a strand comprising the nucleotide sequence completely complementary to the nucleotide sequence of the target forward-strand, and a strand comprising a nucleotide sequence having at least 80%, preferably at least 85%, and more preferably at least 90% homology with such strand.

When PCR is carried out under stringent hybridization conditions using as primers polynucleotide fragments from the composition or kit of the present invention, a PCR buffer comprising 10 mM Tris-HCl (pH 8.3), 50 mM KCl, or 1-2 mM $MgCl_2$, for example, is used to carry out the PCR at a temperature of Tm+5 to 10° C., which is calculated from the primer sequence, for about 15 seconds to 1 minute. The Tm value can be calculated by the equation Tm=2×(the number of adenine residues+the number of thymine residues)+4× (the number of guanine residues+the number of cytosine residues), for example.

Another example of the "stringent conditions" for hybridization is described in Sambrook, J. & Russell, D., Molecular Cloning, A LABORATORY MANUAL, Cold Spring Harbor Laboratory Press, Jan. 15, 2001, vol. 1: 7.42 to 7.45, vol. 2: 8.9 to 8.17, for example, and such conditions can be employed in the present invention.

When quantitative RT-PCR is employed, commercially available assay kits specifically designed to quantitatively assay miRNA, such as TaqMan® MicroRNA Assays, (Life Technologies), LNA™-based MicroRNA PCR (Exiqon), or the Ncode™ miRNA qRT-PCT kit (Invitrogen), may be used.

The present invention also provides a method for predicting the response to Trastuzumab therapy of a breast cancer patient comprising measuring expression levels of the target nucleic acids or genes in samples obtained from breast cancer patients using the composition, kit, or DNA chip of the present invention or any combination thereof, and performing the SVM method using the determined gene expression levels as the training data set.

Specifically, the present invention further provides a method for predicting a response to Trastuzumab therapy of a breast cancer patient comprising the steps of (1) measuring in vitro expression levels of target nucleic acids in a plurality of samples from breast cancer patients who are known to respond to Trastuzumab therapy using the compositions, kits, or DNA chips of the present invention or any combinations thereof;

(2) measuring expression levels of the target nucleic acids obtained in step (1) and preparing a discriminant (a support vector machine) using, as training samples, gene expression levels calculated from the expression levels of the target nucleic acids obtained in step (1);

(3) measuring in vitro expression levels of the target nucleic acids in the sample from a breast cancer patient at the time of surgery or biopsy examination as in step (1); and (4) assigning, to the discriminant determined in step (2), the gene expression levels in breast cancer lesion calculated from the target nucleic acid expression levels determined in step 3, and predicting, determining, or evaluating that the breast cancer patient has a response to Trastuzumab therapy based on the results determined from the discriminant, wherein the target nucleic acids can be detected using the polynucleotides contained in the composition, kit, or DNA chip, mutants thereof, or fragments thereof.

Alternatively, the method of the present invention can comprise, for example, the following steps (a), (b), and (c) of (a) measuring expression levels of target genes in samples obtained from breast cancer patients whose response to Trastuzumab therapy was known, using the composition, kit, or DNA chip for prediction (or determination, detection, or diagnosis) according to the present invention;

(b) assigning the expression levels determined in step (a) to the equations 2 to 5 in accordance with the procedures described below to prepare a discriminant using the SVM method; and (c) measuring expression levels of the target genes in a sample from a breast cancer patient using the composition, kit, or DNA chip for prediction (or determination, detection, or diagnosis) of the present invention, assigning the determined values to the discriminant prepared in step (b), and then predicting a breast cancer patient' response to Trastuzumab therapy based on the results.

SVM is a technique for discriminant analysis invented by V. Vapnik of AT&T in 1995 (The Nature of Statistical Leaning Theory, Springer, 1995). A boundary referred to as a hyperplane for accurate classification of a data set is set by designating particular data elements in the data set in which data are already known to be grouped as explanatory variables and the group to be classified as an objective variable, and a discriminant for classification of the data is determined using such boundary. By assigning measured values of a newly provided data set to the discriminant as the explanatory variable, the discriminant enables prediction of the outcome of grouping. The predicted outcome may be a group to be classified, a probability of t being classified into a group of interest, or a distance from the hyperplane (e.g., Hideki Asou et al., *Toukei kagaku no furontia* 6 (Frontier of statistical science 6), "*Pataan ninshiki to gakushu no toukeigaku* (Statistics of pattern recognition and learning): *atarashii gainen to shuho* (new concepts and procedures)," Iwanami Shoten Publishers, Tokyo, Japan, 2004).

Explanatory variables used with the discriminant by the SVM technique of the present invention include values determined by measuring polynucleotides selected from the polynucleotides described in §2 above or fragments thereof. Specifically, explanatory variables for prediction of a breast cancer patient's response to Trastuzumab therapy according to the present invention are the gene expression levels (1) or (2) below:

(1) the gene expression levels in the breast cancer tissue from a breast cancer patient measured using DNA comprising at least 16 continuous nucleotides in a nucleotide sequence represented by any of SEQ ID NOs: 1 to 9, 11 to 19, and 21 to 23 by substitution of u with t or in a sequence complementary thereto; or (2) the gene expression levels in the breast cancer tissue from a breast cancer patient measured using DNA comprising at least 16 continuous nucleotides in the nucleotide sequence represented by SEQ ID NO: 10 or 20 by substitution of u with t or in a sequence complementary thereto, in addition to DNA comprising at least 16 continuous nucleotides in a nucleotide sequence represented by any of SEQ ID NOs: 1 to 9, 11 to 19, and 21 to 23 by substitution of u with t or in a sequence complementary thereto.

Examples of the computation of a discriminant that can be used in the method of the present invention are described below.

At the outset, breast cancer patients are divided into two groups: a group of patients responding to Trastuzumab therapy; and a group of patients not responding to Trastuzumab therapy. The criteria for judging that a breast cancer patient responds to Trastuzumab therapy can be used as a state showing that the breast cancer progression is inhibited after treatment with Trastuzumab. That is, the result of a pathological examination performed after Trastuzumab therapy is classified as Grade 3 pursuant to the criteria for histological therapeutic effects as defined in the General Rules for Clinical and Pathological Recording of Breast Cancer, the 16th edition, the Japanese Breast Cancer Society (ed.). More specifically, the response to Trastuzumab therapy can be determined when necrosis or quenching of all cancer cells or replacement of all cancer cells with granuloma-like tissue or fibrotic focus is pathologically verified. Alternatively, the response to Trastuzumab therapy can be determined when the result of a pathological examination meets both the criteria; i.e., that no lymph node metastatic focus is clinically verified, in addition that pathological complete response classified as Grade 3 according to the histological therapeutic effects above is verified.

Subsequently, a data set comprising comprehensive gene expression levels in biological samples obtained from the breast cancer tissues of breast cancer patients of the two groups (hereafter referred to as the "training data set") are prepared, and the SVM discriminant using genes exhibiting apparent differences in expression levels between two groups as explanatory variables and the groups as objective variables (e.g., −1 and 1) is determined (Equation 1). The discriminant has a restriction as defined in Equation 2 and a weighting factor (w) and a bias constant (b) as defined in Equations 3 to 5.

Equations 1 to 5 are shown below.

$$f(x) = \sum_{i=1}^{n} w_i \cdot x_i + b \qquad \text{[Equation 1]}$$

wherein x represents a data set comprising comprehensive gene expression levels obtained from biological samples that are derived from breast cancer tissues of breast cancer patients; and xi represents an expression level of a particular gene selected from the data set.

$$y_i(w^T x_i + b) \geq 1 - \xi_i$$

$$\xi_i \geq 0, i=1, \ldots, n \qquad \text{[Equation 2]}$$

wherein T represents an inner product; y represents a classification of data; and ζ represents a slack variable.

$$\sum \alpha_i - \frac{1}{2} \sum \alpha_i \alpha_j y_i y_j x_i^T x_j \qquad \text{[Equation 3]}$$

Equation 3 represents a problem of optimization using Lagrange multipliers (α) led by the use of the Lagrange's method of undetermined multipliers in Equation 2.

$$0 \leq \alpha_i \leq C, \sum_{i=1}^{n} \alpha_i y_i = 0 \qquad \text{[Equation 4]}$$

wherein C represents a limiting condition parameter determined by an experiment.

$$w = \sum_{i=1}^{n} \alpha_i y_i x_i \qquad \text{[Equation 5]}$$

$$b = -\frac{1}{2}(w^T x_A + w^T x_B)$$

Concerning breast cancer patients whose response to Trastuzumab therapy remains unknown, the gene expression levels in the biological samples obtained from the breast cancer tissues of breast cancer patients, which levels are to be used in the discriminant, are measured, and the measured values are assigned to the xi in the discriminant. Thus, the group into which a patient is to be classified can be predicted.

As described above, a discriminant prepared based on the training data set is necessary for preparing an equation that determines whether breast cancer patients whose responses to Trastuzumab therapy remain unknown are classified into the group of patients responding to Trastuzumab therapy or the group of patients not responding to Trastuzumab therapy. In order to improve the prediction accuracy of such discriminant, it is necessary that genes showing apparent differences between the two groups in the training data set are used in the discriminant.

Genes used as the explanatory variables of the discriminant are preferably determined in the following manner. At the outset, the training data set, which is the comprehensive gene expression levels in breast cancer tissue-derived biological samples from breast cancer patients responding to Trastuzumab therapy and the comprehensive gene expression levels in breast cancer tissue-derived biological samples from breast cancer patients not responding to Trastuzumab therapy, is prepared, and differences in expression levels of respective genes between the two groups are determined using p values in the t-test which is a parametric analysis, p values in the Mann-Whitney U-test which is a non-parametric analysis, the rank determined by the rank product method, and the like.

Subsequently, a discriminant is prepared using an arbitrary number of genes exhibiting significant differences in expression levels, and then, gene expression levels in a breast cancer tissue-derived biological sample from another independent breast cancer patient is assigned to the explanatory variable of the discriminant, thereby evaluating a response to Trastuzumab therapy in the breast cancer patient. In order to prepare a discriminant giving maximal prediction accuracy, the preparation of such discriminant and the determination of such prediction accuracy are repeatedly evaluated by increasing genes one by one in the order that a difference in expression levels is large.

It is preferable that the genes used in the discriminant and the prediction accuracy are determined by using the LOOCV method (FIG. 1). Specifically, one datum is first extracted as a test datum from the training data set, and the remnant is designated as the learning data set. A discriminant is then prepared using the learning data set, and the group to which the test datum belongs is predicted using the discriminant. Concerning a plurality of combinations of data, preferably all possible combinations of data, in which a test datum can be separated from the training data without overlapping, a predictive value when the discriminant is used is determined, and then an AUROC value is determined using the predictive value and the actual group to which the test datum belongs, and the determined AUROC value is a prediction accuracy.

Figure 2:
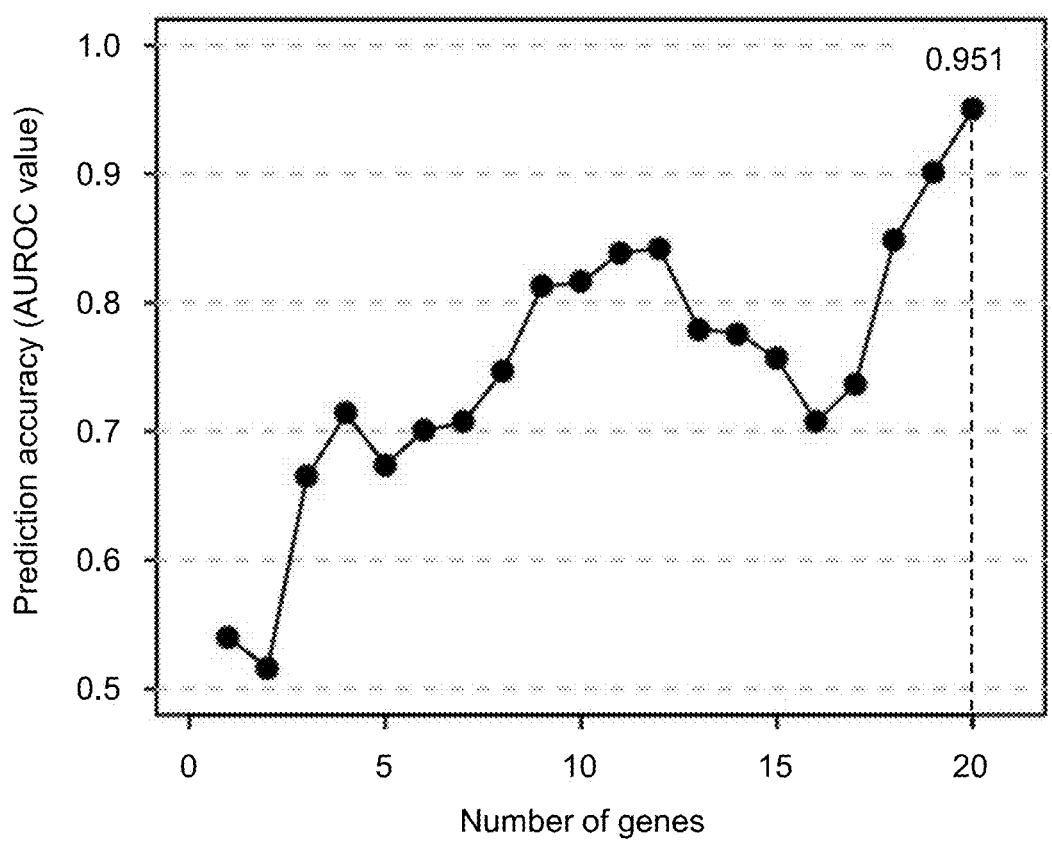
FIG. 2 shows the prediction rate of the response to Trastuzumab therapy in a breast cancer patient when the polynucleotides shown in SEQ ID NOs: 1 to 23 corresponding to the genes shown in Table 1 are used in combination. The vertical axis indicates the AUROC value for the prediction of the response to Trastuzumab therapy in a breast cancer patient, and the horizontal axis indicates the total number of genes, in SEQ ID NOs: 1 to 23 corresponding to the genes shown in Table 1, necessary for prediction of the response to Trastuzumab therapy in breast cancer patients when 35 cases of breast cancer patients are evaluated by the SVM method using the LOOCV method.

According to the method of the present invention, for example, one or more polynucleotides represented by any of SEQ ID NOs: 1 to 23 and/or any combination selected from one or more polynucleotides represented by any of SEQ ID NOs: 1 to 23 are employed to measure expression levels of 23 genes, by using as an indicator that expression levels of the 23 target genes above are different between the group of patients responding to Trastuzumab therapy and the group of patients not responding to Trastuzumab therapy and that the expression levels of the 23 target genes above are increased or decreased in breast cancer lesions from breast cancer patients. Thus, any combination of expression levels of 20 genes is employed to evaluate the response to Trastuzumab therapy in a breast cancer patient with a prediction accuracy of 0.951 as AUROC value (FIG. 2).

EXAMPLES

The present invention is described in more detail with reference to the following examples, although the technical scope of the present invention is not limited to these examples.

Example 1

1. Sample Extraction

From the 35 preoperative primary breast cancer patients, who were diagnosed to be Her2 positive based on the immunohistochemical HER2 staining score 3+, or based on the immunohistochemical HER2 staining score 2+ and the HER2/CEP17 ratio of greater than 2.2 determined by fluorescence in situ hybridization, from whom informed consents had been obtained, breast cancer tissue samples were removed from needle biopsy before Trastuzumab therapy in combination with anticancer agents, and FFPE samples were obtained from the removed breast cancer tissues. Pathological samples of the breast cancer tissues sliced to a thickness of 10 μm were obtained from the FFPE samples.

Specifically, 35 patients with Her2-positive breast cancer were subjected to needle biopsy in order to obtain breast cancer tissue samples before Trastuzumab therapy in combination with anticancer agents. Following needle biopsy, these patients were subjected to Trastuzumab therapy and to preoperative chemotherapy with cyclophosphamide and docetaxel. Therapeutic effects attained with Trastuzumab and the anticancer agents were evaluated using the pathological specimens obtained at the time of surgery. When the pathological complete response classified as Grade 3 pursuant to the criteria for histological therapeutic effects as defined in the General Rules for Clinical and Pathological Recording of Breast Cancer, the 16th edition, the Japanese Breast Cancer Society (ed.) was confirmed and the absence of lymph node metastatic focus was clinically verified, a patient was determined to respond to Trastuzumab therapy.

When the examination method described in Non-Patent Document 3 was employed in accordance with the criteria for evaluation of therapeutic effects, among the 35 patients with Her2-positive breast cancer, 19 patients were found to respond to Trastuzumab therapy in combination with anticancer agents. That is, the prediction accuracy of the examination method according to Non-Patent Document 3 was 54.2%.

2. Extraction of Total RNA

Tissues at breast cancer lesions were cut out from the pathological specimens from the 35 patients with Her2-positive breast cancer, obtained in §1 above using the laser microdissection system (Leica). Total RNA was obtained from the tissues using the Arcturus® Paradise® Plus 2 round amino-allyl kit (Life Technologies) in accordance with the manufacturer's instructions.

3. Measurement of Gene Expression Level

Total RNA samples obtained from the 35 patients with Her2-positive breast cancer in §2 above were subjected to measurement of the gene expression levels using the oligo DNA microarray (3D-Gene® Human miRNA Oligo chip, Toray Industries, Inc.). Measurement on oligo DNA microarray was carried out in accordance with the procedure defined by Toray Industries, Inc., the DNA microarray subjected to hybridization was scanned using the 3D-Gene® scanner (Toray Industries, Inc.) to prepare an image, and the fluorescent intensity was numerically expressed using the 3D-Gene® Extraction (Toray Industries, Inc.). The numerically-expressed fluorescent intensity was converted into a logarithm with the base of 2 so as to be regarded as a gene expression level. Thus, the expression levels of nucleic acid sequences, i.e., comprehensive miRNAs, detected by hybridization with probes on the Human miRNA Oligo chip for the 35 patients with Her2-positive breast cancer, were determined.

4. Prediction Scoring System

The expression levels of miRNAs detected in total RNA samples derived from the breast cancer tissues from the 35 patients with Her2-positive breast cancer obtained in §1. to §3 above were compared among patients based on the clinical information concerning the presence or absence of patients' responses to Trastuzumab therapy obtained in §3 above, to determine the genes used for prediction of the response to Trastuzumab therapy. The prediction accuracy for the response of a patient with Her2-positive breast cancer to Trastuzumab therapy attained with the use of such genes was calculated using the Matlab version 2011a (Mathworks). Specifically, among the 35 patients with Her2-positive breast cancer in §3 above, miRNAs exhibiting the gene expression level 5 or higher in 75% or more patients were selected in accordance with the LOOCV method as shown in FIG. 1. Subsequently, an arbitrary patient was selected from the 35 patients with Her2-positive breast cancer, the miRNA gene expression data for the arbitrary patient were designated as the test data, and the miRNA gene expression data set of other 34 patients was designated as the learning data set. Then, the learning data set was divided into two groups using the clinical information concerning the presence or absence of the response to Trastuzumab therapy in patients with Her2-positive breast cancer as the indicator, and the learning data were subjected to a test for difference between two groups by the rank product method, and the rank of each gene in the learning data set exhibiting the degree of involvement of the gene in the response to Trastuzumab therapy was calculated. Thereafter, a discriminant for predicting the response to Trastuzumab therapy using a type of gene exhibiting the highest rank determined by the rank product method was prepared by the SVM method (Equations 1 to 5), and the response to Trastuzumab therapy of the test data was predicted using the discriminant.

Subsequently, all the other 34 combinations were subjected to the same procedure and, as a result, 35 patterns of predicted responses to Trastuzumab therapy were calculated. The prediction accuracy determined using such 35 types of predictive values and the clinical information concerning the presence or absence of the response of a patient with Her2-positive breast cancer to Trastuzumab therapy obtained in §1 above (i.e., AUROC value) was 0.540, and the gene that was selected at least once from among the 35 combinations was the gene of SEQ ID NO: 1.

In order to further improve the prediction accuracy for the response to Trastuzumab therapy, genes significantly associated with the response to Trastuzumab therapy were used in combination. Specifically, the rank was calculated by the rank product method, a SVM-based discriminant was prepared using two or more genes at the second and subsequent ranks, and the response to Trastuzumab therapy in the test set is predicted using the discriminant in the manner described above. Such procedure is performed on all 35 combinations by the LOOCV method, and the prediction accuracy attained with each number of genes (i.e., AUROC value) was determined.

As a result, the prediction accuracy for the response to Trastuzumab therapy was as follows. The AUROC values were: 0.516 with the use of 2 genes; 0.664 with the use of 3 genes; 0.714 with the use of 4 genes; 0.674 with the use of 5 genes; 0.701 with the use of 6 genes; 0.707 with the use of 7 genes; 0.747 with the use of 8 genes; 0.813 with the use of 9 genes; 0.816 with the use of 10 genes; 0.839 with the use of 11 genes; 0.842 with the use of 12 genes; 0.780 with the use of 13 genes; 0.776 with the use of 14 genes; 0.757 with the use of 15 genes; 0.707 with the use of 16 genes; 0.737 with the use of 17 genes; 0.849 with the use of 18 genes; 0.901 with the use of 19 genes; 0.951 with the use of 20 genes; 0.908 with the use of 21 genes; and 0.885 with the use of 22 genes. That is, the prediction accuracy for the response to Trastuzumab therapy was maximized when 20 genes were used (FIG. 2). The genes that were selected at least once from the 35 types of combinations when such 20 genes were used were the genes of SEQ ID NOs: 1 to 23, and the number of times that the 23 genes were selected in the 35 combinations is as shown in Table 1. This indicates that the prediction accuracy attained using the 20 genes according to the present invention is much higher than that attained by the examination method disclosed in Non-Patent Document 3 (54.2%).

TABLE 1

| SEQ ID NO: | Gene Name | Number of times selected by 35 LOOCVs |
|---|---|---|
| 1 | miR-1234 | 35 |
| 2 | miR-513a-5p | 35 |
| 3 | miR-494 | 35 |
| 4 | miR-26a | 35 |
| 5 | let-7a | 35 |
| 6 | let-7b | 35 |
| 7 | let-7g | 35 |
| 8 | miR-940 | 35 |
| 9 | miR-1470 | 35 |
| 10 | miR-125a-5p | 35 |
| 11 | miR-200c | 35 |
| 12 | let-7e | 35 |
| 13 | miR-1228 | 35 |
| 14 | let-7c | 35 |
| 15 | miR-1229 | 35 |
| 16 | miR-205 | 33 |
| 17 | miR-145 | 33 |
| 18 | miR-181a | 28 |
| 19 | miR-191 | 28 |
| 20 | miR-125b | 23 |
| 21 | miR-92a | 20 |
| 22 | let-7d | 8 |
| 23 | miR-23a | 2 |

Figure 3:
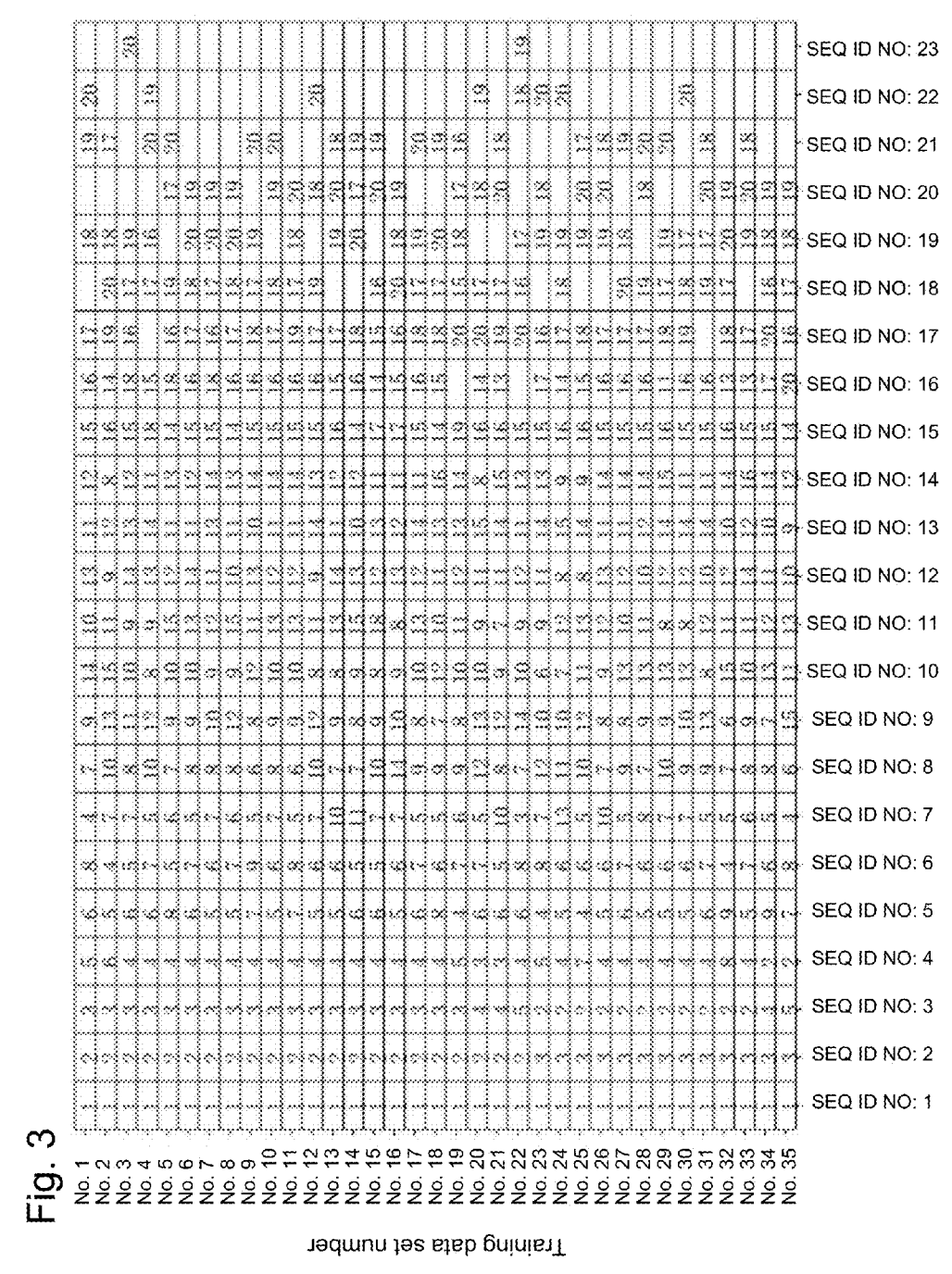

FIG. 3 shows the results of the LOOCV method for selection of 20 types of genes used, when the AUROC value was maximized, for prediction of a breast cancer patient's response to Trastuzumab therapy by the SVM method. Numerical values in the table show the order of priority that is the order that the gene is selected in when the gene for prediction is selected from the training data set. For example, there are 35 ways to select a gene for prediction used when selecting a gene highly involved with response to Trastuzumab therapy from 35 types of training data sets (i.e., when the number of genes is 1 in the chart shown in FIG. 2); however, all the selected 35 genes are SEQ ID NO: 1, and the prediction accuracy for the response to Trastuzumab therapy attained using SEQ ID NO: 1 is as low as 0.540 in terms of the AUROC value. In the 35 types of training data sets exhibiting the highest prediction accuracy (i.e., the AUROC value) of 0.951, in which 34 cases are to be selected from 35 cases, combinations of 20 genes highly involved with the response to Trastuzumab therapy are the following 13 combinations: SEQ ID NOs: 1 to 20; SEQ ID NOs: 1 to 19 and 21; SEQ ID NOs: 1 to 19 and 22; SEQ ID NOs: 1 to 19 and 23; SEQ ID NOs: 1 to 18, 20 and 21; SEQ ID NOs: 1 to 18, 20 and 22; SEQ ID NOs: 1 to 17 and 19 to 21; SEQ ID NOs: 1 to 17, 19, 20 and 22; SEQ ID NOs: 1 to 17, 19, 21 and 22; SEQ ID NOs: 1 to 16 and 18 to 21; SEQ ID NOs: 1 to 16, 18, 19, 21 and 22; SEQ ID NOs: 1 to 15 and 17 to 21; and SEQ ID NOs: 1 to 15, 17 to 19, 22 and 23. That is, genes for prediction used when selecting 20 genes from the training data set (i.e., when the number of genes is 20 in the chart shown in FIG. 2) are 23 genes represented by SEQ ID NOs: 1 to 23.

When the number of genes selected from each training data set (i.e., the number of genes shown in the chart in FIG. 2) is from 1 to 20, the genes for prediction (SEQ ID NOs:) and the prediction accuracy attained using such genes (the AUROC values) are as shown in Table 2.

least number of genes that enables prediction of a response to Trastuzumab with higher accuracy than conventional techniques.

1. Extraction of Samples from 48 Patients

From the 48 preoperative primary breast cancer patients, who were diagnosed to be Her2 positive based on the immunohistochemical HER2 staining score 3+, or based on the immunohistochemical HER2 staining score 2+ and the HER2/CEP17 ratio of greater than 2.2 determined by fluorescence in situ hybridization, from whom informed consents had been obtained, breast cancer tissue samples were removed by needle biopsy before Trastuzumab therapy in combination with anticancer agents, and FFPE samples were obtained from the removed breast cancer tissues. Pathological samples of the breast cancer tissues sliced to a thickness of 10 μm were obtained from the FFPE samples.

Specifically, 48 patients with Her2-positive breast cancer were subjected to needle biopsy in order to obtain breast cancer tissue samples before Trastuzumab therapy in combination with anticancer agents. Following needle biopsy, these patients were subjected to Trastuzumab therapy and to preoperative chemotherapy with fluorouracil, epirubicin,

TABLE 2

| Number of genes selected from each training data set (the number of genes shown in the chart of FIG. 2) | SEQ ID NOs: of genes for prediction selected from each training data set | Prediction accuracy (AUROC value) |
| --- | --- | --- |
| 1 | 1 | 0.540 |
| 2 | 1, 2, 3, 4 | 0.516 |
| 3 | 1, 2, 3, 4, 7 | 0.664 |
| 4 | 1, 2, 3, 4, 5, 6, 7 | 0.714 |
| 5 | 1, 2, 3, 4, 5, 6, 7 | 0.674 |
| 6 | 1, 2, 3, 4, 5, 6, 7, 8, 9, 10 | 0.701 |
| 7 | 1, 2, 3, 4, 5, 6, 7, 8, 9, 10, 11 | 0.707 |
| 8 | 1, 2, 3, 4, 5, 6, 7, 8, 9, 10, 11, 12, 14 | 0.747 |
| 9 | 1, 2, 3, 4, 5, 6, 7, 8, 9, 10, 11, 12, 13, 14 | 0.813 |
| 10 | 1, 2, 3, 4, 5, 6, 7, 8, 9, 10, 11, 12, 13, 14 | 0.816 |
| 11 | 1, 2, 3, 4, 5, 6, 7, 8, 9, 10, 11, 12, 13, 14, 16 | 0.839 |
| 12 | 1, 2, 3, 4, 5, 6, 7, 8, 9, 10, 11, 12, 13, 14, 16 | 0.842 |
| 13 | 1, 2, 3, 4, 5, 6, 7, 8, 9, 10, 11, 12, 13, 14, 16 | 0.780 |
| 14 | 1, 2, 3, 4, 5, 6, 7, 8, 9, 10, 11, 12, 13, 14, 15, 16 | 0.776 |
| 15 | 1, 2, 3, 4, 5, 6, 7, 8, 9, 10, 11, 12, 13, 14, 15, 16, 17, 18 | 0.757 |
| 16 | 1, 2, 3, 4, 5, 6, 7, 8, 9, 10, 11, 12, 13, 14, 15, 16, 17, 18, 19, 21 | 0.707 |
| 17 | 1, 2, 3, 4, 5, 6, 7, 8, 9, 10, 11, 12, 13, 14, 15, 16, 17, 18, 19, 20, 21 | 0.737 |
| 18 | 1, 2, 3, 4, 5, 6, 7, 8, 9, 10, 11, 12, 13, 14, 15, 16, 17, 18, 19, 20, 21, 22 | 0.849 |
| 19 | 1, 2, 3, 4, 5, 6, 7, 8, 9, 10, 11, 12, 13, 14, 15, 16, 17, 18, 19, 20, 21, 22, 23 | 0.901 |
| 20 | 1, 2, 3, 4, 5, 6, 7, 8, 9, 10, 11, 12, 13, 14, 15, 16, 17, 18, 19, 20, 21, 22, 23 | 0.951 |

As described above, the number of genes giving the highest AUROC value in predicting the breast cancer patient's response to Trastuzumab therapy is 20, as shown in the chart in FIG. 2. The genes used for prediction are 23 genes of SEQ ID NOs: 1 to 23 shown in Table 2.

Example 2

When predicting the breast cancer patient's response to Trastuzumab therapy using the SEQ ID NOs: 1 to 23, the prediction accuracy for the group of 35 patients with Her2-positive breast cancer as the subject in Example 1 and that for the group of 48 independent patients different therefrom were confirmed, in order to determine the combination of the cyclophosphamide, and docetaxel. Therapeutic effects attained with Trastuzumab and the anticancer agents were evaluated using the pathological specimens obtained at the time of surgery. When the pathological complete response classified as Grade 3 pursuant to the criteria for histological therapeutic effects as defined in the General Rules for Clinical and Pathological Recording of Breast Cancer, the 16th edition, the Japanese Breast Cancer Society (ed.) was confirmed and the absence of lymph node metastatic focus was clinically verified as in Example 1, a patient was determined to respond to Trastuzumab therapy.

When the examination method described in Non-Patent Document 3 was employed in accordance with the criteria for evaluation of therapeutic effects, among the 48 patients with Her2-positive breast cancer, 20 patients were found to respond to Trastuzumab therapy in combination with anti-cancer agents. That is, the prediction accuracy of the examination method according to Non-Patent Document 3 was 41.7%.

2. Extraction of Total RNA from Samples of 48 Patients

Tissues at breast cancer lesions were cut out from the pathological specimens from the 48 patients with Her2-positive breast cancer, obtained in §1 above using the laser microdissection system (Leica), as in Example 1, §2. Total RNA was obtained from the tissues using the Arcturus® Paradise® Plus 2 round amino-allyl kit (Life Technologies) in accordance with the manufacturer's instructions.

3. Measurement of Gene Expression Level in Samples of 48 Patients

Total RNA samples obtained from the 48 patients with Her2-positive breast cancer in §2 above were subjected to measurement of the gene expression levels using the oligo DNA microarray (3D-Gene® Human miRNA Oligo chip, Toray Industries, Inc.), as in Example 1, §2. Measurement on oligo DNA microarray was carried out in accordance with the procedure defined by Toray Industries, Inc., the DNA microarray subjected to hybridization was scanned using the 3D-Gene® scanner (Toray Industries, Inc.) to prepare an image, and the fluorescent intensity was numerically expressed using the 3D-Gene® Extraction (Toray Industries, Inc.). The numerically-expressed fluorescent intensity was converted into a logarithm with the base of 2 so as to be regarded as a gene expression level. Thus, the expression levels of nucleic acid sequences, i.e., comprehensive miRNAs, detected by hybridization with probes on the Human miRNA Oligo chip for the 48 patients with Her2-positive breast cancer, were determined.

4. Prediction Scoring System

The gene expression levels of miRNAs (SEQ ID NOs: 1 to 23) detected from total RNAs from the breast cancer tissues of the 35 patients with Her2-positive breast cancer obtained in Example 1, §1 to §3 above were compared among patients based on the clinical information concerning the presence or absence of patients' responses to Trastuzumab therapy obtained in Example 1, §3 above. A prediction scoring system for predicting the response of a patient with Her2-positive breast cancer to Trastuzumab therapy with the use of two genes arbitrarily selected from among the miRNAs (SEQ ID NOs: 1 to 23) was prepared using Matlab version 2011a (Mathworks).

Specifically, one arbitral patient was selected from the 35 patients with Her2-positive breast cancer, the miRNA gene expression datum of the arbitral patient was designated as a test datum, and the miRNA gene expression data set of other 34 patients was designated as the learning data set. Subsequently, the learning data set was divided into two groups using the clinical information concerning the presence or absence of the response to Trastuzumab therapy of patients with Her2-positive breast cancer as the indicator, a discriminant for the prediction of the response to Trastuzumab therapy using any two genes selected from miRNAs represented by SEQ ID NOs: 1 to 23 was prepared by the SVM method (Equations 1 to 5), and the response to Trastuzumab therapy of the test data was predicted using the discriminant. Subsequently, all the other 34 combinations were subjected to the same procedure and, as a result, 35 types of predictive values concerning the response to Trastuzumab therapy were determined, and the prediction accuracy concerning the 35 patients (i.e., AUROC values) was determined.

In the end, the AUROC values were determined with respect to all combinations of two genes selected from miRNAs represented by SEQ ID NOs: 1 to 23 concerning the 35 patients, and the combinations of two genes giving the prediction accuracy higher than that of the examination method described in Non-Patent Document 3 (i.e., 65.2%) and the prediction accuracy thereof were determined.

5. Prediction of Response to Trastuzumab Therapy Using Two Genes Selected from SEQ ID NOs: 1 to 23

The miRNA gene expression levels detected in total RNAs derived from the breast cancer tissues from the 48 patients in Example 2, §1 to Example 2, §3 were determined using the prediction scoring system prepared using combinations of two genes selected from miRNAs (SEQ ID NOs: 1 to 23). The accuracy for prediction of the responses of the patients with Her2-positive breast cancer to Trastuzumab therapy performed using such prediction scoring system was determined for all combinations of two genes using Matlab version 2011a (Mathworks).

As a result, combinations of two genes selected from the genes (SEQ ID NOs: 1 to 23) determined in Example 1 that give a high prediction accuracy for the responses to Trastuzumab therapy of both the group of 35 patients with Her2-positive breast cancer employed in Example 1 and the group of 48 patients with Her2-positive breast cancer as the subject in Example 2 and the prediction accuracy thereof are as shown in Table 3. Specifically, the prediction accuracy attained using the combinations of two genes as shown in Table 3 according to the present invention is significantly higher than the prediction accuracy of the examination method described in Non-Patent Document 3 examined for the 35 patients with Her2-positive breast cancer in Example 1 (i.e., 54.2%) and that for the 48 patients with Her2-positive breast cancer in Example 2 (i.e., 41.7%).

TABLE 3

| Combination for selecting 2 genes from 23 genes | | Prediction results for 35 cases | Prediction results for 48 cases |
|---|---|---|---|
| SEQ ID NO: | SEQ ID NO: | AUROC value | AUROC value |
| 4 | 6 | 0.671 | 0.686 |
| 4 | 12 | 0.658 | 0.657 |
| 5 | 6 | 0.678 | 0.681 |
| 5 | 11 | 0.655 | 0.684 |
| 5 | 17 | 0.678 | 0.688 |
| 5 | 20 | 0.668 | 0.680 |
| 5 | 23 | 0.681 | 0.717 |
| 6 | 7 | 0.671 | 0.684 |
| 6 | 9 | 0.674 | 0.698 |
| 6 | 10 | 0.655 | 0.679 |
| 6 | 12 | 0.664 | 0.686 |
| 6 | 15 | 0.678 | 0.696 |
| 6 | 17 | 0.664 | 0.663 |
| 6 | 21 | 0.671 | 0.680 |
| 6 | 23 | 0.694 | 0.664 |

INDUSTRIAL APPLICABILITY

The present invention can provide a composition used for prediction of the response to Trastuzumab therapy in breast cancer patients with high prediction accuracy. Accordingly, the present invention is very effective for prediction of the breast cancer patient's response to Trastuzumab therapy alone or in combination with anticancer agents.

The invention claimed is:

1. A method for predicting response to Trastuzumab therapy in an HER 2 positive breast cancer patient and treating with Trastuzumab the same HER2 positive breast cancer patient, comprising:
   predicting response to Trastuzumab therapy by the following steps of:
   (i) measuring, by hybridization or RT-PCR analysis, expression levels of target nucleic acids let-7a of SEQ ID NO: 5 and miR-23a of SEQ ID NO: 23 in a breast cancer tissue sample from the breast cancer patient using two or more polynucleotides selected from the group consisting of the following (a) to (b):
   (a) polynucleotides each comprising a nucleotide sequence having 95% or higher identity with the nucleotide sequence of SEQ ID NOs: 5 or 23 or with a nucleotide sequence derived therefrom by substitution of u with t, or fragments thereof comprising at least 16 continuous nucleotides; and
   (b) polynucleotides each comprising a nucleotide sequence complementary to the nucleotide sequence having 95% or higher identity with the nucleotide sequence of SEQ ID NOs: 5 or 23 or with a nucleotide sequence derived therefrom by substitution of u with t, or fragments thereof comprising at least 16 continuous nucleotides; and
   (ii) assigning the expression levels determined by measurement in step (i) to a discriminant prepared by a support vector machine using expression levels of target nucleic acids let-7a of SEQ ID NO: 5 and miR-23a of SEQ ID NO: 23 in a plurality of breast cancer tissue samples from breast cancer patients who are known to respond to Trastuzumab therapy and in a plurality of samples from breast cancer patients who are known not to respond to Trastuzumab therapy, wherein the expression levels are measured using the two or more polynucleotides or fragments thereof as defined in the (a) to (b), thereby predicting the patient is responsive to Trastuzumab therapy;
   administering Trastuzumab in a therapeutically effective amount to the breast cancer patient with predicted Trastuzumab therapy response.

2. The method according to claim 1, wherein measuring, by hybridization or RT-PCR analysis, expression levels of target nucleic acids let-7a of SEQ ID NO: 5 and miR-23a of SEQ ID NO: 23 in a breast cancer tissue sample from the breast cancer patient comprises using a DNA chip comprising the two or more polynucleotides of the polynucleotides and/or fragments thereof as defined in (a) to (b) of claim 1.

* * * * *